(12) United States Patent
Zucherman et al.

(10) Patent No.: US 8,491,653 B2
(45) Date of Patent: Jul. 23, 2013

(54) INTERVERTEBRAL BODY FUSION CAGE WITH KEELS AND IMPLANTATION METHODS

(75) Inventors: James F. Zucherman, San Francisco, CA (US); Ken Y. Hsu, San Francisco, CA (US); Henry A. Klyce, Piedmont, CA (US); Charles J. Winslow, Walnut Creek, CA (US); Scott Yerby, Montara, CA (US); Steve Mitchell, Pleasant Hill, CA (US); John Flynn, Concord, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 312 days.

(21) Appl. No.: 12/924,741

(22) Filed: Oct. 4, 2010

(65) Prior Publication Data

US 2011/0022176 A1    Jan. 27, 2011

Related U.S. Application Data

(62) Division of application No. 10/993,005, filed on Nov. 19, 2004, now Pat. No. 7,837,732.

(60) Provisional application No. 60/537,382, filed on Jan. 16, 2004, provisional application No. 60/523,604, filed on Nov. 20, 2003.

(51) Int. Cl.
*A61F 2/44* (2006.01)

(52) U.S. Cl.
USPC .................................................... 623/17.11

(58) Field of Classification Search
USPC .............................. 606/246; 623/17.11–17.16
See application file for complete search history.

(56) References Cited

U.S. PATENT DOCUMENTS

| | | |
|---|---|---|
| 190,061 A | 4/1877 | Middleton |
| 200,860 A | 3/1878 | French |
| 1,418,758 A | 6/1922 | Watkins |
| 1,486,295 A | 3/1924 | Mullen |
| 1,905,498 A | 4/1933 | Pfeiffer |
| 2,677,369 A | 5/1954 | Knowles |
| 3,298,372 A | 1/1967 | Feinberg |
| 3,848,601 A | 11/1974 | Ma et al. |
| 3,867,728 A | 2/1975 | Stubstad et al. |
| 3,875,595 A | 4/1975 | Froning |
| 3,880,414 A | 4/1975 | Smith et al. |
| 3,916,907 A | 11/1975 | Peterson |
| 3,987,499 A | 10/1976 | Scharbach et al. |
| 4,044,170 A | 8/1977 | Scharbach et al. |
| 4,064,567 A | 12/1977 | Burstein et al. |
| 4,262,369 A | 4/1981 | Roux |
| 4,309,777 A | 1/1982 | Patil |
| 4,349,921 A | 9/1982 | Kuntz |
| 4,401,112 A | 8/1983 | Rezaian |
| 4,484,570 A | 11/1984 | Sutter et al. |

(Continued)

FOREIGN PATENT DOCUMENTS

| | | |
|---|---|---|
| DE | 2263842 | 7/1974 |
| DE | 2365873 | 8/1976 |

(Continued)

*Primary Examiner* — Nicholas Woodall

(57) ABSTRACT

An intervertebral implant has a fusion body with at least one keel that anchors the implant into cancellous bone of at least one vertebral body. A method for implantation includes lateral implantation of the implant.

25 Claims, 20 Drawing Sheets

U.S. PATENT DOCUMENTS

| | | |
|---|---|---|
| 4,501,269 A | 2/1985 | Bagby |
| RE31,865 E | 4/1985 | Roux |
| 4,537,185 A | 8/1985 | Stednitz |
| 4,545,374 A | 10/1985 | Jacobson |
| 4,553,273 A | 11/1985 | Wu |
| 4,599,086 A | 7/1986 | Doty |
| 4,611,581 A | 9/1986 | Steffee |
| 4,636,217 A | 1/1987 | Ogilvie et al. |
| 4,677,972 A | 7/1987 | Tornier |
| 4,714,469 A | 12/1987 | Kenna |
| 4,743,256 A | 5/1988 | Brantigan |
| 4,759,766 A | 7/1988 | Buettner-Janz et al. |
| 4,772,287 A | 9/1988 | Ray et al. |
| 4,820,305 A | 4/1989 | Harms et al. |
| 4,834,757 A | 5/1989 | Brantigan |
| 4,863,476 A | 9/1989 | Shepperd |
| 4,863,477 A | 9/1989 | Monson |
| 4,878,915 A | 11/1989 | Brantigan |
| 4,901,987 A | 2/1990 | Greenhill et al. |
| 4,904,261 A | 2/1990 | Dove et al. |
| 4,911,718 A | 3/1990 | Lee et al. |
| 4,917,704 A | 4/1990 | Frey et al. |
| 4,932,969 A | 6/1990 | Frey et al. |
| 4,936,848 A | 6/1990 | Bagby |
| 4,946,378 A | 8/1990 | Hirayama et al. |
| 4,950,270 A | 8/1990 | Bowman et al. |
| 4,955,908 A | 9/1990 | Frey et al. |
| 4,961,740 A | 10/1990 | Ray et al. |
| 4,997,432 A | 3/1991 | Keller |
| 5,002,576 A | 3/1991 | Fuhrmann et al. |
| 5,011,484 A | 4/1991 | Breard |
| 5,015,247 A | 5/1991 | Michelson |
| 5,015,255 A | 5/1991 | Kuslich |
| 5,026,373 A | 6/1991 | Ray et al. |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,071,437 A | 12/1991 | Steffee |
| 5,108,438 A | 4/1992 | Stone |
| 5,123,926 A | 6/1992 | Pisharodi |
| 5,147,402 A | 9/1992 | Bohler et al. |
| 5,171,278 A | 12/1992 | Pisharodi |
| 5,171,281 A | 12/1992 | Parsons et al. |
| 5,192,326 A | 3/1993 | Bao et al. |
| 5,192,327 A | 3/1993 | Brantigan |
| 5,246,458 A | 9/1993 | Graham |
| 5,258,043 A | 11/1993 | Stone |
| 5,263,953 A | 11/1993 | Bagby |
| 5,282,861 A | 2/1994 | Kaplan |
| 5,306,308 A | 4/1994 | Gross et al. |
| 5,306,309 A | 4/1994 | Wagner et al. |
| 5,314,477 A | 5/1994 | Marnay |
| 5,314,478 A | 5/1994 | Oka et al. |
| 5,320,644 A | 6/1994 | Baumgartner |
| 5,397,364 A | 3/1995 | Kozak et al. |
| 5,401,269 A | 3/1995 | Buttner-Janz et al. |
| 5,403,136 A | 4/1995 | Mathys |
| 5,423,817 A | 6/1995 | Lin |
| 5,424,773 A | 6/1995 | Saito |
| 5,425,772 A | 6/1995 | Brantigan |
| 5,443,514 A | 8/1995 | Steffee |
| 5,458,638 A | 10/1995 | Kuslich et al. |
| 5,489,307 A | 2/1996 | Kuslich et al. |
| 5,489,308 A | 2/1996 | Kuslich et al. |
| 5,505,732 A | 4/1996 | Michelson |
| 5,514,180 A | 5/1996 | Heggeness et al. |
| 5,522,899 A | 6/1996 | Michelson |
| 5,534,031 A | 7/1996 | Matsuzaki et al. |
| 5,554,191 A | 9/1996 | Lahille et al. |
| 5,556,431 A | 9/1996 | Buttner-Janz |
| 5,571,189 A | 11/1996 | Kuslich |
| 5,571,190 A | 11/1996 | Ulrich et al. |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,645,596 A | 7/1997 | Kim et al. |
| 5,645,598 A | 7/1997 | Brosnahan, III |
| 5,653,761 A | 8/1997 | Pisharodi |
| 5,653,762 A | 8/1997 | Pisharodi |
| 5,653,763 A | 8/1997 | Errico et al. |
| 5,658,336 A | 8/1997 | Pisharodi |
| 5,658,337 A | 8/1997 | Kohrs et al. |
| 5,665,122 A | 9/1997 | Kambin |
| 5,669,909 A | 9/1997 | Zdeblick et al. |
| 5,676,701 A | 10/1997 | Yuan et al. |
| 5,683,463 A | 11/1997 | Godefroy et al. |
| 5,683,465 A | 11/1997 | Shinn et al. |
| 5,709,683 A | 1/1998 | Bagby |
| 5,716,415 A | 2/1998 | Steffee |
| 5,766,252 A | 6/1998 | Henry et al. |
| 5,782,832 A | 7/1998 | Larsen et al. |
| 5,782,919 A | 7/1998 | Zdeblick et al. |
| D397,439 S | 8/1998 | Koros et al. |
| 5,865,845 A | 2/1999 | Thalgott |
| 5,865,847 A | 2/1999 | Kohrs et al. |
| 5,885,287 A | 3/1999 | Bagby |
| 5,888,223 A | 3/1999 | Bray, Jr. |
| 5,895,428 A | 4/1999 | Berry |
| 5,899,941 A | 5/1999 | Nishijima et al. |
| 5,904,719 A | 5/1999 | Errico et al. |
| 5,906,616 A | 5/1999 | Pavlov et al. |
| 5,947,971 A | 9/1999 | Kuslich et al. |
| 5,968,098 A | 10/1999 | Winslow |
| 5,980,552 A | 11/1999 | Pinchasik et al. |
| 5,989,291 A | 11/1999 | Ralph et al. |
| 6,019,792 A | 2/2000 | Cauthen |
| 6,063,121 A | 5/2000 | Xavier et al. |
| 6,102,950 A | 8/2000 | Vaccaro |
| 6,111,164 A | 8/2000 | Rainey et al. |
| 6,113,637 A | 9/2000 | Gill et al. |
| 6,113,638 A * | 9/2000 | Williams et al. ............ 128/898 |
| 6,117,174 A | 9/2000 | Nolan |
| 6,123,705 A | 9/2000 | Michelson |
| 6,129,763 A | 10/2000 | Chauvin et al. |
| 6,156,067 A | 12/2000 | Bryan et al. |
| 6,159,245 A | 12/2000 | Meriwether et al. |
| 6,165,219 A | 12/2000 | Kohrs et al. |
| 6,168,631 B1 | 1/2001 | Maxwell et al. |
| 6,176,882 B1 | 1/2001 | Biedermann et al. |
| 6,179,874 B1 | 1/2001 | Cauthen |
| 6,206,922 B1 | 3/2001 | Zdeblick et al. |
| 6,224,631 B1 | 5/2001 | Kohrs |
| 6,290,724 B1 | 9/2001 | Marino |
| 6,306,170 B2 | 10/2001 | Ray |
| 6,325,827 B1 | 12/2001 | Lin |
| 6,332,894 B1 | 12/2001 | Stalcup et al. |
| 6,368,350 B1 | 4/2002 | Erickson et al. |
| 6,395,035 B2 | 5/2002 | Bresina et al. |
| 6,413,278 B1 | 7/2002 | Marchosky |
| 6,428,575 B2 | 8/2002 | Koo et al. |
| 6,436,139 B1 | 8/2002 | Shapiro et al. |
| 6,440,170 B1 | 8/2002 | Jackson |
| 6,443,989 B1 | 9/2002 | Jackson |
| 6,454,807 B1 | 9/2002 | Jackson |
| 6,517,580 B1 | 2/2003 | Ramadan et al. |
| 6,572,653 B1 | 6/2003 | Simonson |
| 6,579,318 B2 | 6/2003 | Varga et al. |
| 6,582,467 B1 | 6/2003 | Teitelbaum et al. |
| 6,592,624 B1 | 7/2003 | Fraser et al. |
| 6,613,090 B2 | 9/2003 | Eckhof et al. |
| 6,613,091 B1 | 9/2003 | Zdeblick et al. |
| 6,648,915 B2 | 11/2003 | Sazy |
| 6,682,563 B2 | 1/2004 | Scharf |
| 6,699,288 B2 | 3/2004 | Moret |
| 6,706,068 B2 | 3/2004 | Ferree |
| 6,706,070 B1 | 3/2004 | Wagner et al. |
| 6,716,245 B2 | 4/2004 | Pasquet et al. |
| 6,740,118 B2 | 5/2004 | Eisermann et al. |
| 6,743,255 B2 | 6/2004 | Ferree |
| 6,743,256 B2 | 6/2004 | Mason |
| 6,764,491 B2 | 7/2004 | Frey et al. |
| 6,773,460 B2 | 8/2004 | Jackson |
| 6,790,233 B2 | 9/2004 | Brodke et al. |
| 6,835,206 B2 | 12/2004 | Jackson |
| 6,835,208 B2 | 12/2004 | Marchosky |

| | | |
|---|---|---|
| 6,893,464 B2 | 5/2005 | Kiester |
| 6,926,737 B2 | 8/2005 | Jackson |
| 6,936,071 B1 | 8/2005 | Marnay et al. |
| 6,953,477 B2 * | 10/2005 | Berry ................ 623/17.11 |
| 6,966,929 B2 | 11/2005 | Mitchell |
| 6,972,019 B2 | 12/2005 | Michelson |
| 7,048,766 B2 | 5/2006 | Ferree |
| 7,056,344 B2 | 6/2006 | Huppert et al. |
| 7,060,073 B2 | 6/2006 | Frey et al. |
| 7,063,725 B2 * | 6/2006 | Foley ................ 623/17.16 |
| 7,112,222 B2 | 9/2006 | Fraser et al. |
| 7,137,997 B2 | 11/2006 | Paul |
| 7,235,101 B2 | 6/2007 | Berry et al. |
| 7,331,995 B2 | 2/2008 | Eisermann et al. |
| 7,682,397 B2 * | 3/2010 | Berry et al. ............ 623/17.14 |
| 2002/0016592 A1 | 2/2002 | Branch et al. |
| 2002/0040243 A1 | 4/2002 | Attali et al. |
| 2002/0065560 A1 | 5/2002 | Varga et al. |
| 2002/0116066 A1 | 8/2002 | Chauvin et al. |
| 2002/0193881 A1 | 12/2002 | Shapiro et al. |
| 2003/0083748 A1 | 5/2003 | Lee et al. |
| 2003/0167091 A1 | 9/2003 | Scharf |
| 2003/0181981 A1 | 9/2003 | Lemaire |
| 2004/0024462 A1 | 2/2004 | Ferree et al. |
| 2004/0117022 A1 | 6/2004 | Marnay et al. |
| 2004/0122518 A1 | 6/2004 | Rhoda |
| 2004/0143330 A1 | 7/2004 | Sazy |
| 2004/0148028 A1 | 7/2004 | Ferree et al. |
| 2004/0220668 A1 | 11/2004 | Eisermann et al. |
| 2004/0225366 A1 | 11/2004 | Eisermann et al. |
| 2004/0249465 A1 | 12/2004 | Ferree |
| 2004/0249466 A1 | 12/2004 | Liu et al. |
| 2004/0254643 A1 | 12/2004 | Jackson |
| 2004/0260286 A1 | 12/2004 | Ferree |
| 2005/0021145 A1 | 1/2005 | de Villiers et al. |
| 2005/0043800 A1 | 2/2005 | Paul et al. |
| 2005/0085917 A1 | 4/2005 | Marnay et al. |
| 2005/0113916 A1 | 5/2005 | Branch, Jr. |
| 2005/0113926 A1 | 5/2005 | Zucherman et al. |
| 2005/0143821 A1 | 6/2005 | Zdeblick et al. |
| 2005/0143822 A1 | 6/2005 | Paul |
| 2005/0159756 A1 | 7/2005 | Ray |
| 2005/0261772 A1 | 11/2005 | Filippi et al. |
| 2005/0267581 A1 | 12/2005 | Marnay et al. |
| 2005/0288788 A1 | 12/2005 | Dougherty-Shah |
| 2006/0036325 A1 | 2/2006 | Paul et al. |
| 2006/0106460 A1 | 5/2006 | Messerli et al. |
| 2006/0206207 A1 | 9/2006 | Dryer et al. |
| 2006/0212118 A1 | 9/2006 | Abernathie |

FOREIGN PATENT DOCUMENTS

| | | |
|---|---|---|
| DE | 2910627 | 9/1980 |
| DE | 29911422 U1 | 9/1999 |
| EP | 0042271 | 12/1981 |
| EP | 0179695 | 4/1986 |
| EP | 0307241 | 3/1989 |
| EP | 0328847 | 8/1989 |
| EP | 0551187 | 7/1993 |
| EP | 0566810 A1 | 10/1993 |
| EP | 0599419 | 6/1994 |
| EP | 0637440 | 2/1995 |
| EP | 0716840 | 6/1996 |
| EP | 0732093 | 9/1996 |
| EP | 0734703 | 10/1996 |
| FR | 2372622 | 6/1978 |
| FR | 2636227 | 3/1990 |
| FR | 2718635 | 10/1995 |
| WO | WO 93/10725 | 6/1993 |
| WO | WO 94/04100 | 3/1994 |
| WO | WO 95/00082 | 1/1995 |
| WO | WO 96/40020 | 12/1996 |
| WO | WO 98/38924 | 9/1998 |
| WO | WO 01/01893 A1 | 1/2001 |
| WO | WO 01/64142 A1 | 9/2001 |
| WO | WO 02/03895 A1 | 1/2002 |

\* cited by examiner

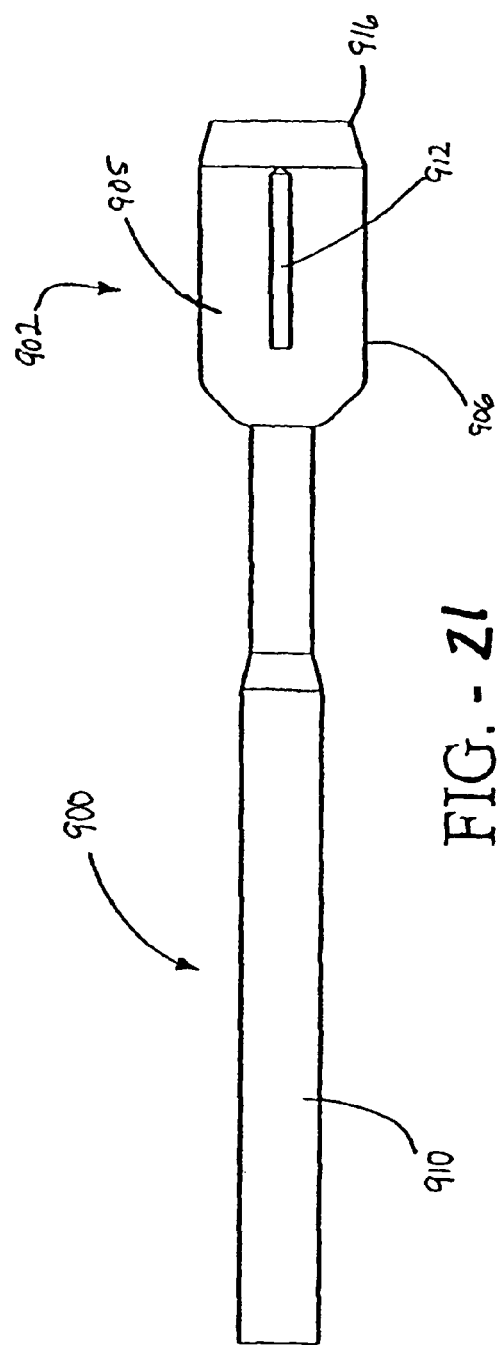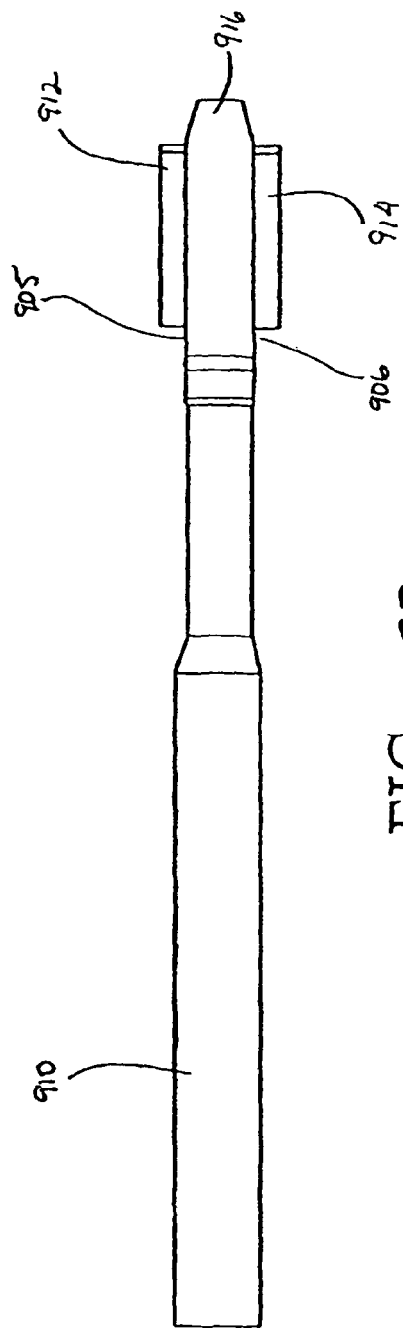
FIG. - 21
FIG. - 22

INTERVERTEBRAL BODY FUSION CAGE WITH KEELS AND IMPLANTATION METHODS

CROSS REFERENCE TO RELATED APPLICATIONS

This application is a divisional of U.S. patent application Ser. No. 10/993,005 filed Nov. 19, 2004 now U.S. Pat. No. 7,837,732, which claims the benefit of U.S. Provisional Patent Application No. 60/537,382 filed Jan. 16, 2004 and U.S. Provisional Patent Application No. 60/523,604 filed Nov. 20, 2003, the contents of each application hereby incorporated by reference in its entirety.

FIELD OF THE INVENTION

This invention relates to an intervertebral body fusion cage.

BACKGROUND OF THE INVENTION

The spinal column is a biomechanical structure composed primarily of ligaments, muscles, vertebrae, and intervertebral disks. The biomechanical functions of the spine include: (1) support of the body, which involves the transfer of the weight and the bending movements of the head, trunk and arms to the pelvis and legs; (2) complex physiological motion between these parts; and (3) protection of the spinal cord and nerve roots.

As the present society ages, it is anticipated that there will be an increase in adverse spinal conditions which are characteristic of aging. For example, with aging comes an increase in spinal stenosis (including, but not limited to, central canal and lateral stenosis), and facet joint degeneration. In addition to spinal stenosis and facet joint degeneration, the incidence of damage to the intervertebral disks is also common.

The primary purpose of the intervertebral disk is to act as a shock absorber. The disk is constructed of an inner gel-like structure, the nucleus pulposus (the nucleus), and an outer rigid structure comprised of collagen fibers, the annulus fibrosus (the annulus). At birth, the disk is 80% water, but the water content gradually diminishes with time, causing the disk to stiffen. With age, disks may degenerate and bulge, thin, herniate, or ossify. Damage to disks also may occur as a result of disease, trauma, or injury to the spine.

Disk damage can have far-reaching consequences. By way of example only, both the cervical and lumbar areas of the human spine are, in a healthy state, normally lordotic such that they are curved convex forward. It is not uncommon that in degenerative conditions of the spine, normal curvature is lost. Loss of normal curvature effectively shortens the spinal canal, and decreases its capacity. Further, the absence or loss of normal curvature of the spine moves the spinal cord to a more anterior position, potentially resulting in compression of the posterior portions of the vertebral bodies and the disks. Loss of normal curvature thus disturbs the overall mechanics of the spine, which may cause cascading degenerative changes throughout the adjacent spinal segments.

The surgical treatment of those degenerative conditions of the spine in which the spinal disks are in various states of collapse commonly involves spinal fusion, that is, the joining together of adjacent vertebrae through an area of shared bone. When the shared bone is in the area previously occupied by the intervertebral disk, the fusion is referred to as an "interbody fusion." Fusion results in formation of a solid bony mass between adjacent vertebral bodies. The newly formed bony mass can assume a weight-bearing function and thereby relieve mechanical pain caused by an unstable degenerative disk. The bony fusion mass further can prevent long-term disk collapse or additional degenerative changes.

Fusion can be accomplished by interbody bone grafting. Typically, grafting requires penetrating the vertebral endplates, which are made of hard bone, to prepare the target vertebrae. Such preparation exposes the spongy, vascular, cancellous bone. Bone grafts then are positioned to be in contact with the cancellous bone and the blood supply. The direct contact between the natural or synthetic bone fragments, with or without other bone growth-promoting materials such as growth factors, initiates a controlled healing process, which results in production of new bone and healing of the graft to both opposed vertebral surfaces. The final result is a single, continuous segment of bone that is composed of the new bony mass between, and fused with, two contiguous vertebrae. Fusion is expected to have a higher probability of success with more direct and extensive contact between the bone graft-promoting materials and the cancellous bone.

Since fusion takes place over time, the spine can remain unstable until fusion is complete. However, spinal instability may contribute to the failure of the fusion. Therefore, a fusion implant is needed that (1) maximizes the probability of success of bone fusion; (2) provides instant stability to the spine while fusion occurs; and (3) is easily implantable and minimizes trauma to the patient and the possibility of surgical and post-surgical complications.

BRIEF DESCRIPTION OF THE DRAWINGS

FIG. 21 is a top view of an embodiment of a disclosed keel-receiving channel cutting tool.

FIG. 22 is a side view of the embodiment of the disclosed keel-receiving channel cutting tool depicted in FIG. 20.

DETAILED DESCRIPTION OF THE PREFERRED EMBODIMENTS OF THE INVENTION

The following description is presented to enable any person skilled in the art to make and use what is disclosed. Various modifications to the embodiments described will be readily apparent to those skilled in the art, and the principles defined herein can be applied to other embodiments and applications without departing from the spirit and scope of what is disclosed and defined by the appended claims. Thus, what is disclosed is not intended to be limited to the embodiments shown, but is to be accorded the widest scope consistent with the principles and features disclosed herein. To the extent necessary to achieve a complete understanding of what is disclosed herein, the specification and drawings of all patents and patent applications cited in this application are incorporated herein by reference.

Unless otherwise stated, each of the embodiments of the implant of the invention described herein can be implanted from a lateral approach, and also from a posterior or anterior approach, using the appropriate surgical technique.

Figure 1:
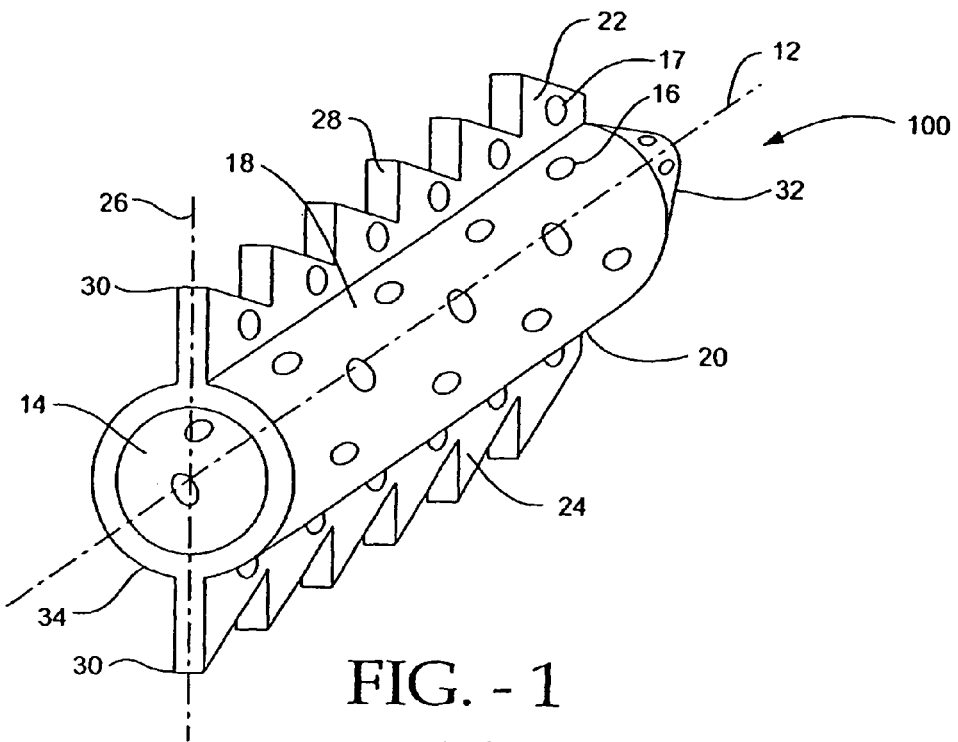
FIG. 1 is a perspective view of an embodiment of the disclosed implant of the invention.
Figure 2:
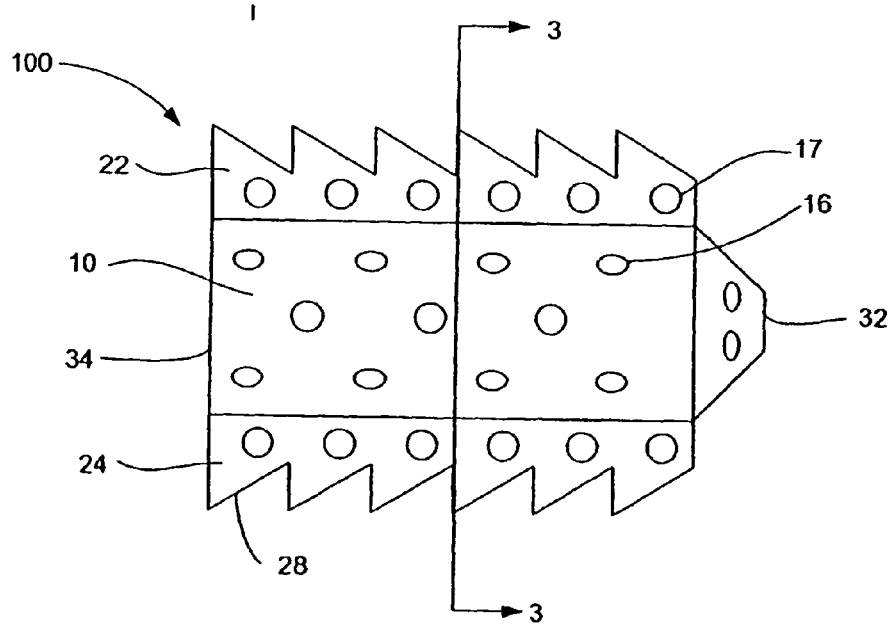
FIG. 2 is a side view of an embodiment of the disclosed implant of the invention of FIG. 1.
Figure 3:
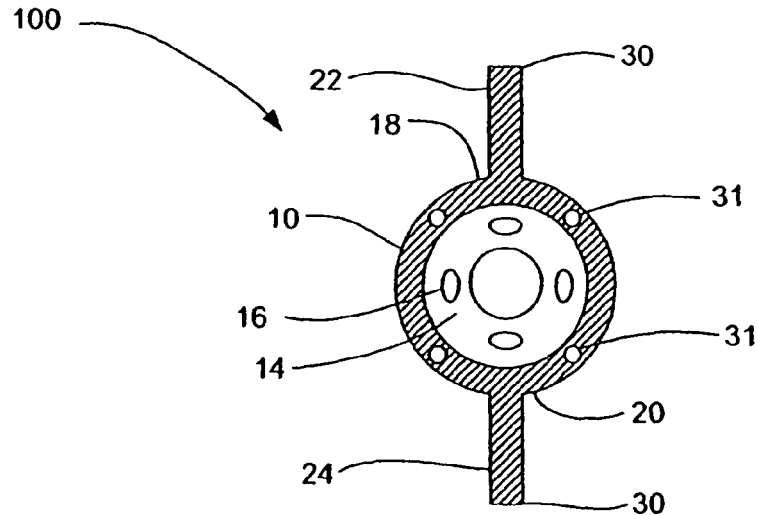
FIG. 3 is a cross-sectional view of the embodiment of the disclosed implant of the invention depicted in FIG. 1.

FIGS. 1-3 depict one embodiment 100 of the disclosed implant. The implant is a fusion cage, adapted to stabilize the affected spine immediately, once anchored in keel-receiving channels cut into the cancellous bone of adjacent vertebral bodies, and to promote bony fusion between the adjacent vertebrae.

This embodiment 100 of the disclosed implant includes a cylindrical cage 10 with a hollow interior 14. The hollow interior 14 is adapted to contain a graft of bone growth-promoting material, to initiate formation of a bony fusion mass between two affected vertebrae. The bone growth-promoting material can include, but is not limited to, naturally occurring bone, bone chips, processed bone, synthetic bone, hydroxyapatite, calcium phosphate compounds, naturally occurring bone morphogenic proteins, natural, synthetic, and recombinant bone morphogenic proteins, growth factors, and cytokines.

The hollow interior 14 and the graft materials contained therein are in communication with the exterior of the cage (i.e., the intervertebral space, the vertebral endplates, and the cancellous bone of the affected vertebrae) through a plurality of apertures 16 configured over the surface of the cage 10 that fully penetrate the surface. It is to be understood that the apertures 16 are to be shaped, sized, and configured over the surface so as to optimize bony ingrowth without compromising the strength of the cage 10. In addition to, or in place of apertures, the surfaces of the cage 10 can be roughened and/or covered with bone growth promoting substances to induce and promote bone growth and integration of the cage 10 into the adjacent vertebrae. The surfaces of the cage 10 further can have a plurality of projections or teeth 28 oriented to further guard against backward expulsion of the implant 100 from the intervertebral space.

The cylindrical cage 10 has a superior surface 18 that abuts the upper vertebra of the two affected vertebrae, and an inferior surface 20 that abuts the lower vertebra. In this embodiment 100, a first keel 22, preferably substantially perpendicular to the sagittal plane of the body, extends along the longitudinal axis 12 of the cylindrical cage 10, and into the cancellous bone of the vertebral body of the top vertebra through a keel-receiving channel cut into the vertebral body of the top vertebra. Similarly, a second keel 24, preferably substantially perpendicular to the sagittal plane of the body, extends along the longitudinal axis 12 of the cylindrical cage 10, and into the cancellous bone of the vertebral body of the bottom vertebra through a keel-receiving channel cut into the vertebral body of the bottom vertebra. The keels include apertures 17 that allow the patient's vertebral bone to grow through to further stabilize and integrate the implant 100 into the upper and lower vertebral bodies that are to fused together.

The keels 22, 24 serve to stabilize the affected spine immediately upon implantation. Further, because they extend beyond the vertebral endplate and into the cancellous bone of the vertebral body, the keels 22, 24 expose the more vascularized bone tissue of the vertebrae to the implant 100. In addition to the apertures 17, the keels 22, 24 can be roughened and/or the keels can be coated with bone growth-promoting materials as described above. Additionally, the other surfaces of the implant 100 can be so treated. The keels 22, 24 therefore not only stabilize the spine, but also serve to enhance bone growth and fusion of the affected contiguous vertebrae.

It is to be understood that the keels 22, 24 need not extend the full length of the longitudinal axis 12 of the cylindrical cage 10. Moreover, although this embodiment 100 of the disclosed implant only has two keels 22, 24, it is also within the scope of the present disclosure to have a plurality of keels along the same longitudinal axis 12 of the cage, as described herein below, or along parallel longitudinal axes.

Figure 3A:
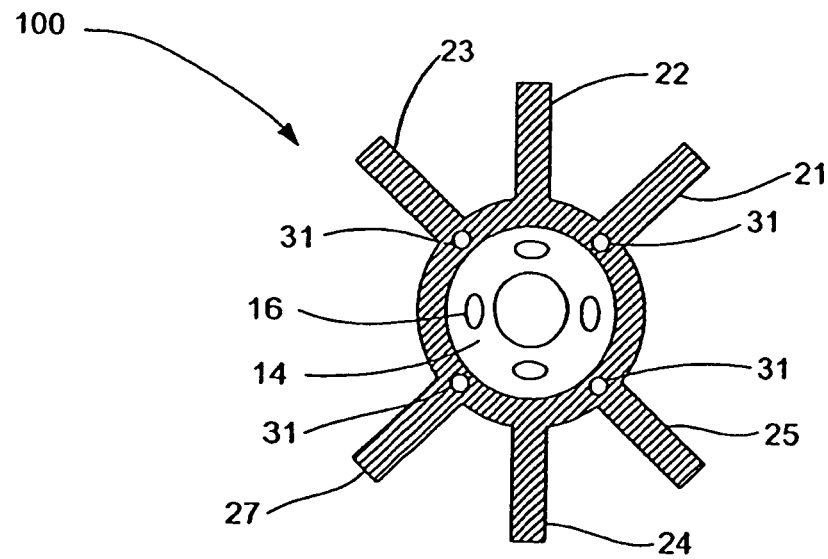
FIG. 3A is a view similar to FIG. 3 of an alternative embodiment of the implant of the invention.
Figure 3B:
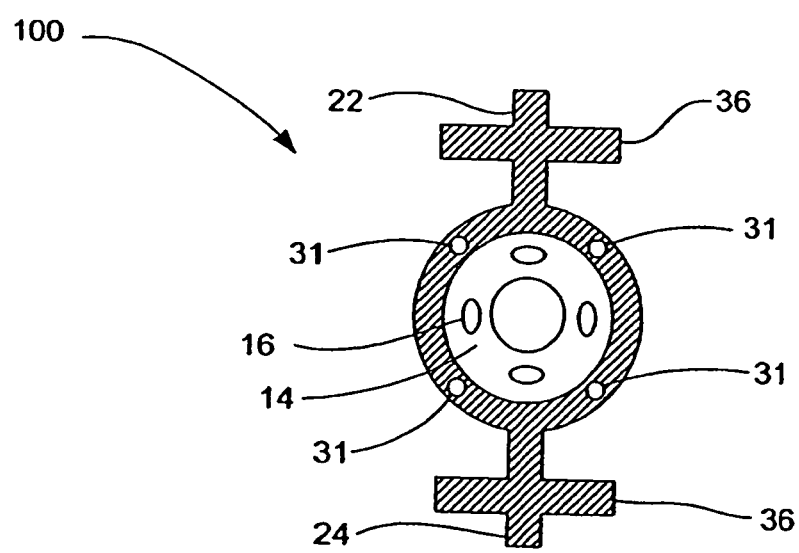
FIG. 3B is a view similar to FIG. 3 of an alternative embodiment of the implant of the invention.

As depicted in FIGS. 3A and 3b the keels can have different configurations. In FIG. 3A the implant 100 includes a plurality of keels 22 extending from the superior surface 18 and a plurality of keels 24 extending from the inferior surface 20. Overall, the keels 22, 24 form a somewhat star pattern. The keels can be of different lengths with the center keels 22, 24 being longer and the right and left side keels 21, 23 and 25, 27 respectively, being shorter. In addition, each keel can have teeth 28 and apertures 17 as described above, in the context of describing the other keels. These keels also can be roughened and/or covered with bone growth-promoting substances. Such additional keels may allow for stabilization of the implant into the adjacent vertebral bodies.

It is further within the scope of this disclosure for the keels 22, 24 to have an extension 36 from the end of the keel that is distal to the cage 10. The extension 36 can be substantially perpendicular to a vertical axis 26 of the keels 22, 24. In other words, the extension 36 creates a keel that has a "T" shape, or an inverted "T"-shape, depending upon the surface of the cage from which the keel 22, 24 extends, in a cross-section perpendicular to the vertical axis 26 of the keel 22, 24. The "T"-shape provides an additional surface area of support for the spongy cancellous bone in which the keels 22, 24 become embedded upon implantation. Thus as depicted in FIG. 3B, the implant 100 includes keels 22, 24 that are in cross-section are shaped like a cross or "T"-shaped in order to include additional surfaces for stabilizing the vertebral bodies and allowing for bone ingrowth.

Each keel 22, 24 further can have a plurality of projections or teeth 28 extending from the end of the keel distal to the cage 10, and from the top of the extension 36. Any projections 28 are oriented at an angle that will guard against backward expulsion of the implant 100 from the intervertebral space.

It is within the scope of this disclosure for the cage 10 to have a tapered first end 32 of the cylindrical cage 10, that serves as the leading end 32. The tapered leading end 32 may facilitate insertion of the implant between the two affected vertebrae, while the vertebrae are distracted apart, if necessary, to accommodate the implant 100. The tapered leading end 32 can be closed, to retain the graft materials remain inside the cage 10. The cage 10 further can be sealed at a second end 34, which is the trailing end, and also the end of the cage 10 through which the graft material is received into the hollow interior 14. A cap, not shown, can be used to seal the second end 34.

The second end 34 also can be adapted operably to connect with a surgical instrument for implantation, not shown. By way of example only, the second/trailing end 34 can have at least one hole 31 adapted to receive at least one pin extending from a first end of a surgical implantation instrument. The hole/pin combination operably connects the implant with the implantation tool, and the latter is used to position the implant within the intervertebral space. Positioning the implant will include aligning at least one keel with a keel-receiving channel cut into at least one vertebra. The implantation step would occur after first exposing the target contiguous vertebrae; removing the affected disk if necessary; distracting the target vertebrae, if necessary; creating keel-receiving channels in the vertebral bodies; and filling the implant with the graft materials, either prior to of after the implant is inserted between the vertebral bodies. As the implant preferably is inserted laterally, along a line that is preferably substantially perpendicular to the sagittal plane of the patient's body, the keels also enter laterally and can add stability in the sagittal plane, the plane where flexion and extension occurs. This method is described in greater detail below.

The cylindrical cage 10 can be made from a variety of materials, including but not limited to bioceramics; calcium phosphate ceramics, such as hydroxyapatite tricalcium phosphate, tetracalcium phosphate, α-calcium pyrophosphate, β-calcium pyrophosphate and mixtures thereof; and ceramic/growth factor composites, such as ceramic/bone morphogenic protein ("BMP") composite (made with any BMP, whether natural, synthetic, or recombinant). The implant also can be made of medical grade titanium, stainless steel or cobalt chrome. Other materials that have appropriate structural strength and that are suitable for implantation into a patient can also be used.

One other class of materials contemplated for use is the class of biocompatible polymers. Copolymers, blends and composites of polymers are also contemplated for fabrication of parts of the disclosed device. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer.

One group of biocompatible polymers is the polyaryl ester ketones which has several members, which include polyetheretherketone (PEEK), and polyetherketoneketone (PEKK). PEEK has proven as a durable material for implants, as well as meeting criteria of biocompatibility. Medical grade PEEK is available from Victrex Corporation under the product name PEEK-OPTIMA. Medical grade PEKK is available from Oxford Performance Materials under the name OXPEKK, and also from CoorsTek under the name Bio-PEKK. Still another interesting group of biocompatible polymers is the polyalkyl biocompatible polymers, such as polyethylenes, polypropylenes, and the like.

These medical grade biocompatible polymers also are available as reinforced polymer materials. To reinforce a polymeric material, fillers are added to a polymer, copolymer, polymer blend, or polymer composite. Fillers are added to modify properties, such as mechanical, optical, and thermal properties. In this case, fillers, such as carbon fibers, are added to reinforce the polymers mechanically to enhance strength for certain uses, such as load bearing devices.

Figure 4:
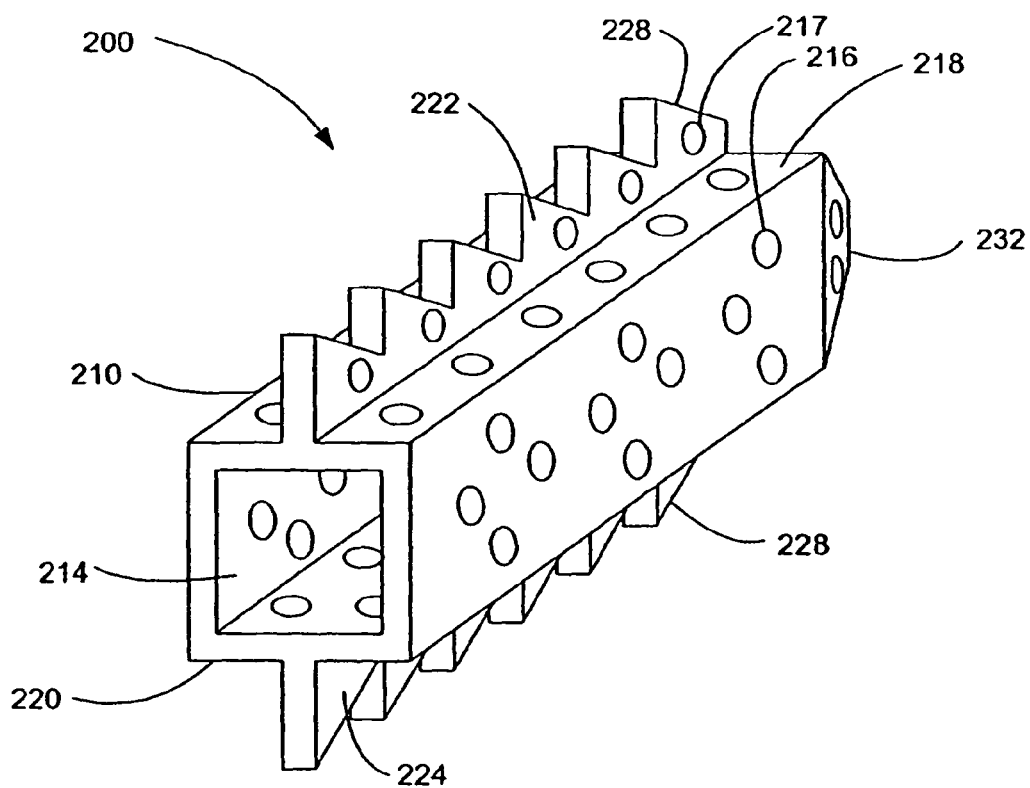
FIG. 4 is a perspective view of a further embodiment of the disclosed implant of the invention.
Figure 5:
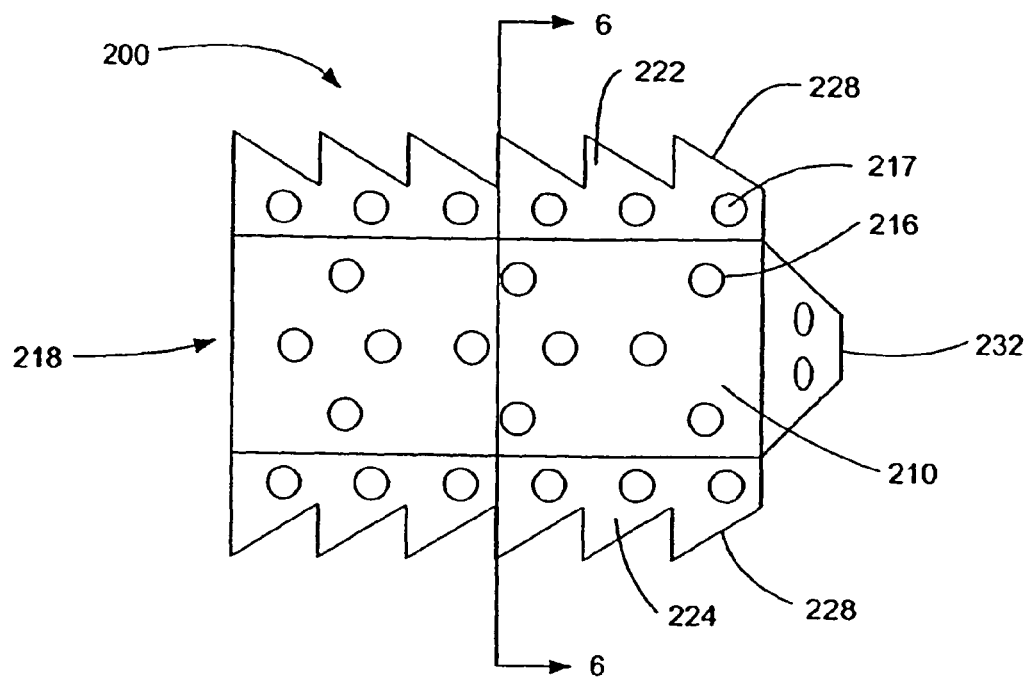
FIG. 5 is a side view of the embodiment of the disclosed implant depicted in FIG. 4.
Figure 6:
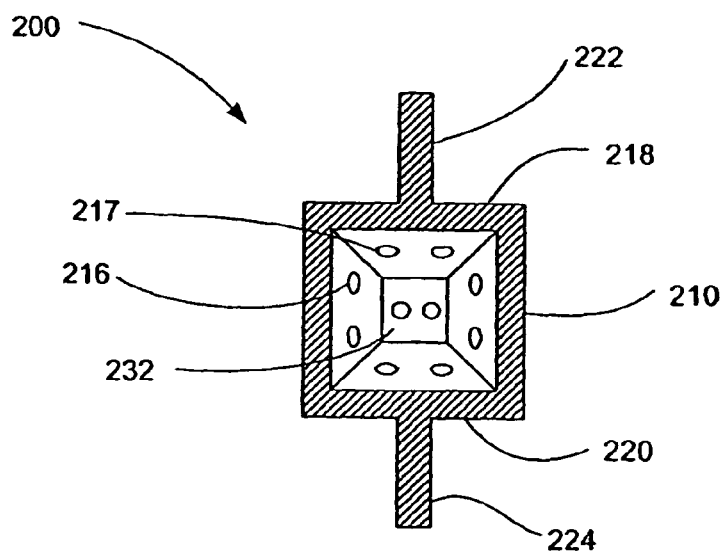
FIG. 6 is a cross-sectional view of the embodiment of the disclosed implant depicted in FIG. 4.

FIGS. 4-6 depict an embodiment 200 of the disclosed implant having a cage 210 with a cubical configuration. The cubical configuration can enhance the communication of the bone graft and bone growth-promoting contents contained in the hollow interior 214 of the cubical cage 210 by bringing a greater surface area of the cage 210, and hence, a greater amount of bone graft material, into direct contact with the cancellous bone of the vertebral bodies. Further the flat superior 218 and inferior 220 planar surfaces of the cage 210 create stabilizing surfaces that mate with the upper and lower end plates of the upper and lower vertebrae. It is to be understood that, for all embodiments, the vertebrae may be somewhat shaped in order to accept the superior 218 and inferior 220 planar surfaces of the cage 210.

As with the embodiments previously described, a plurality of keels 222, 224 is contemplated, extending from the superior 218 and inferior 220 surfaces of the cage 210 of the implant. The keels 222, 224 can have a perpendicular extension (not shown), a plurality of projections or teeth 228 to guard against expulsion backward from the direction of insertion, and a plurality of apertures 217.

The cage 210 has a hollow interior 214 as above, that is in communication with the exterior of the cage via a plurality of apertures 216 that fully penetrate the surface of the cage 210. The embodiment 200 further can have a tapered leading end 232, and an open trailing end 234 for receiving at least one type of bone growth-promoting materials. As with all of the embodiments described herein, the surfaces of the cage 210 can be roughened and/or covered with bone growth promoting substances and/or have apertures in order to induce bone growth and integration of the cage 210 into the adjacent vertebrae. Further, as with all of the embodiments, implant 200 can be made of any one or any combination of materials as described above and can be packed with any one or any combination of the bone growth-promoting substances described herein.

Figure 7:
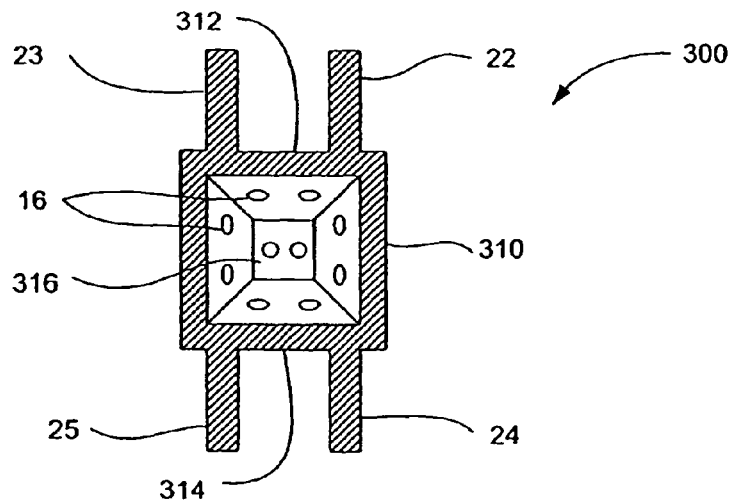
FIG. 7 is a cross-sectional view of a further embodiment of the disclosed implant of the invention.

FIG. 7 depicts a further embodiment of the disclosed implant having two keels 322 on the superior surface 318 of the cage 310, and two keels 324 on the inferior surface 320 of a cubical cage 310. It is further within the scope of this disclosure to have a plurality of keels 322, 324 on the superior 318 and inferior 320 surfaces of the cage 310 irrespective of the shape of the cage. The keels 322, 324 further can have an extension (not shown) substantially perpendicular to the vertical axis 326 of the keel, extending from the end of the keel distal to the cage 310. The keels 322, 324 can extend the full length of the longitudinal axis of the cage 310. Alternatively, the keels 322, 324 can be shorter. Several keels 322, 324 can be aligned along one longitudinal axis, and/or several can be aligned along parallel longitudinal axes.

Figure 8:
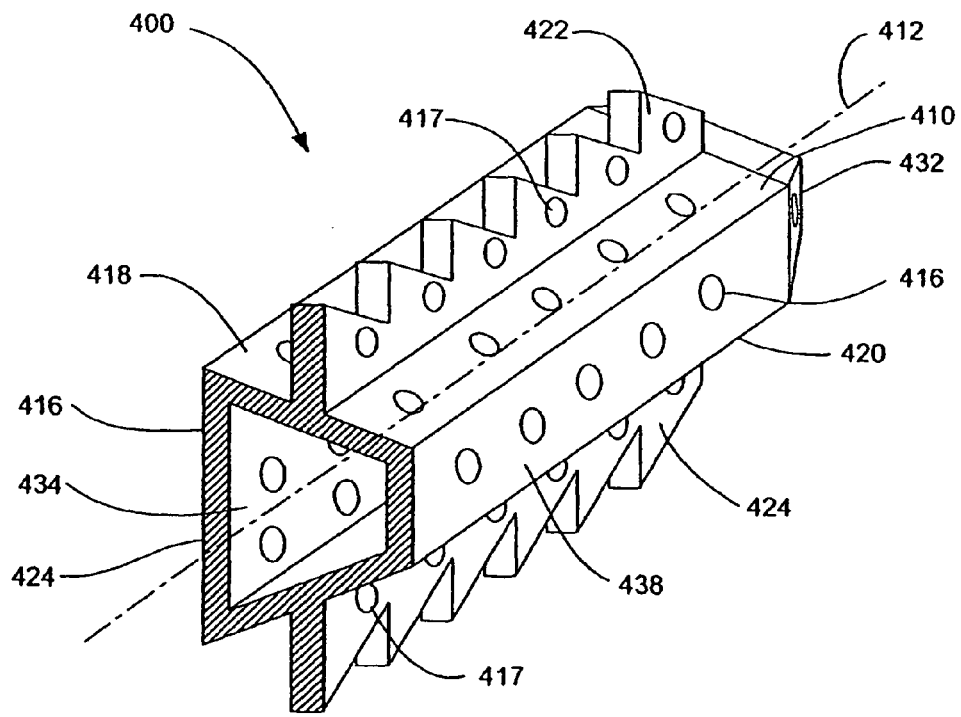
FIG. 8 is a perspective view of a further embodiment of the disclosed implant of the invention.
Figure 9:
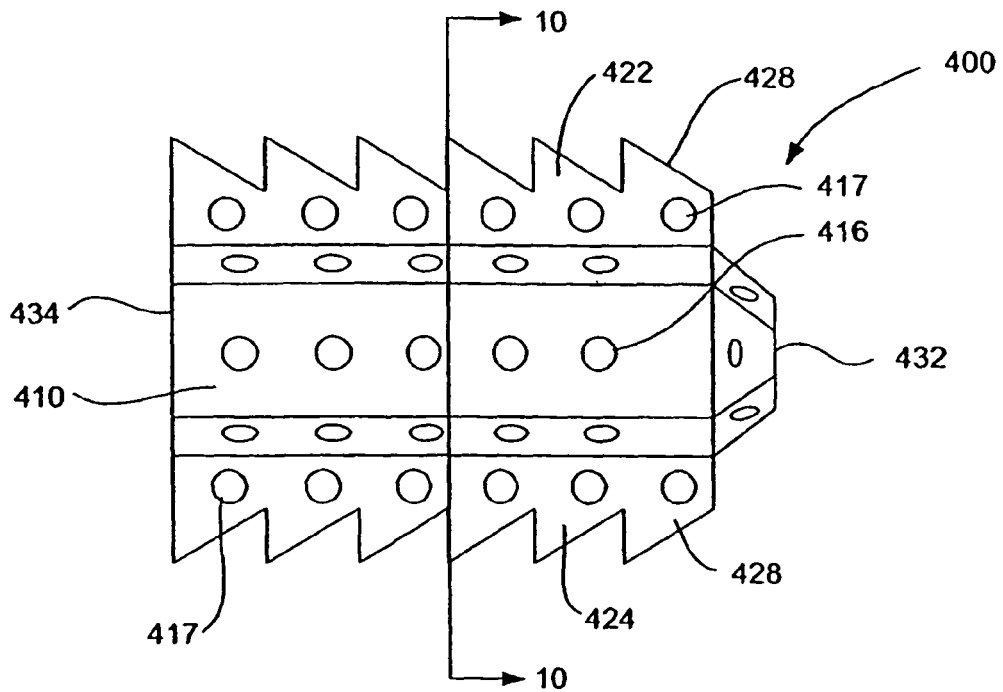
FIG. 9 is a side view of the embodiment of the disclosed implant depicted in FIG. 8.
Figure 10:
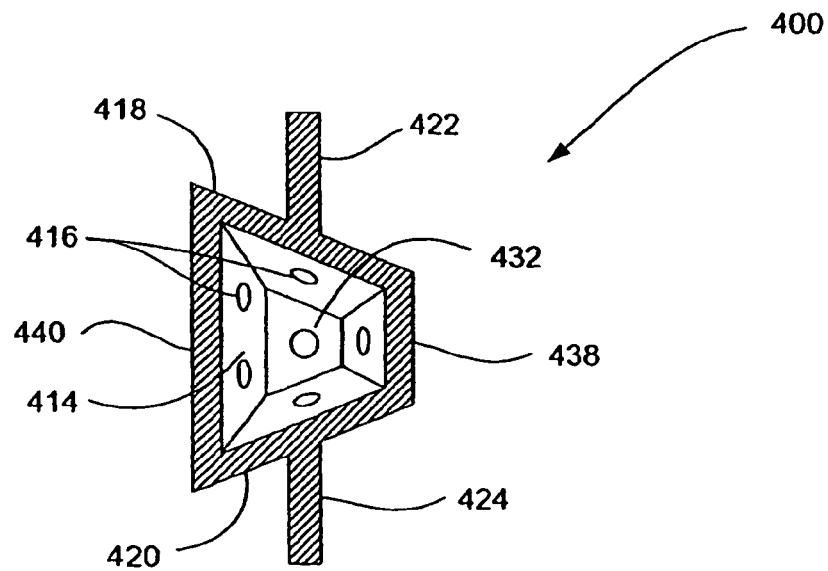
FIG. 10 is a cross-sectional view of the embodiment of the disclosed implant depicted in FIG. 8.

FIGS. 8-10 depict a further embodiment 400 of the disclosed implant. This embodiment 400 has a wedge-shape for correcting curvature of the spine.

In a healthy state, the cervical and lumbar spines normally have a lordotic curvature. In degenerative conditions of the spine, normal such normal curvature can be lost. The loss of anatomical curvature effectively shortens the spinal canal and thereby decreases its capacity. The absence of normal curvature also moves the spinal cord so that it becomes compressed against the posterior sections of the vertebral bodies and disks. Loss of anatomical curvature disturbs the overall mechanics of the spine, and the disruption may cause cascading degenerative changes throughout the adjacent spinal segments.

A wedge-shaped implant 400 with keels 422, 424 implanted from a lateral approach can be used to correct the loss of curvature from a degenerated region of the spine. It is within the scope of this disclosure to have wedge-shaped implants 400 that can return the anatomical curvature to the spine, while also promoting bone fusion as described for the other embodiments above. These embodiments 400 can have apertures 416 through the surfaces of the wedge-shaped cage 410, and/or roughened surfaces, and/or bone growth-promoting substances on their surfaces to induce and promote bone ingrowth and fuse the affected vertebrae. They also can have apertures 417 through the keels 422, 424 extending from the superior 418 and inferior 420 surfaces of the cage 410. The keels 422, 424 can have a plurality of projections or teeth 428 to protect against expulsion of the implant.

The cage 410 is wedge-shaped in a plane that is perpendicular to the longitudinal axis 412 of the cage 410. The narrowest 438 and the widest 440 surfaces of the wedge-shaped cage 410 run parallel to the longitudinal axis of the cage 412 and are opposite each other, rather than adjacent surfaces. Such implants can be manufactured so that a given wedge-shaped cage 410 has an angular dimension that can be custom-selected for a patient's specific needs and anatomy. Moreover, the keels 422, 424 can provide instant stability upon being embedded in keel-receiving channels cut into the cancellous bone of at least one vertebral body and therefore, the correction to return normal curvature to the spine is immediate.

It should be appreciated that embodiment 400 also can be implanted from an anterior or posterior approach. Either of those approaches would correct lateral curvature of the spine.

Figure 11:
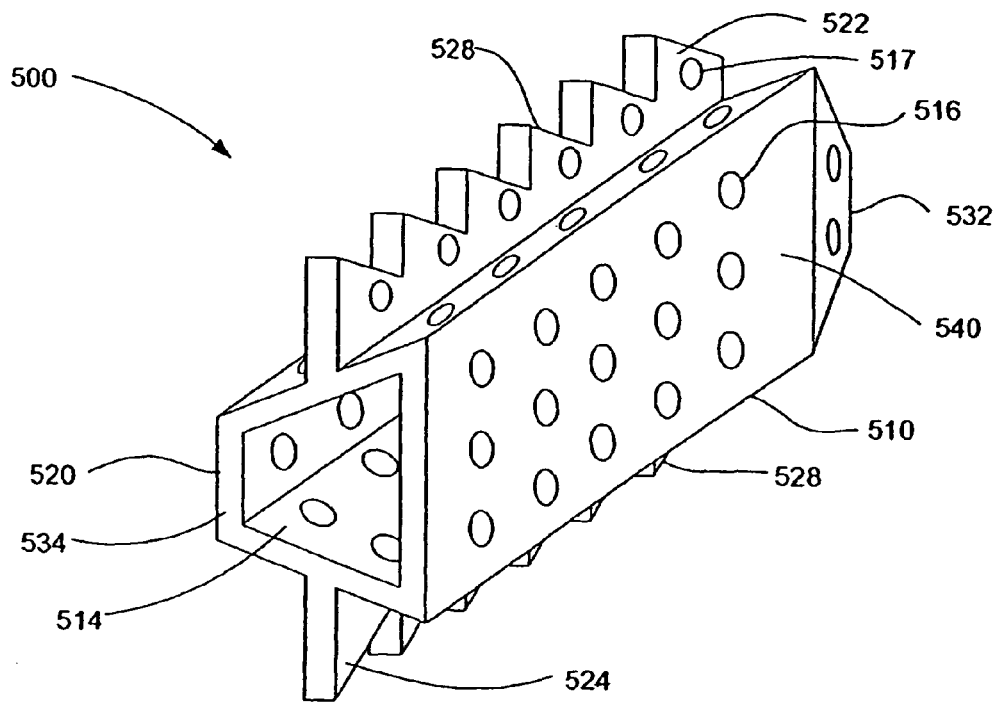
FIG. 11 is a perspective view of a further embodiment of the disclosed implant.
Figure 12:
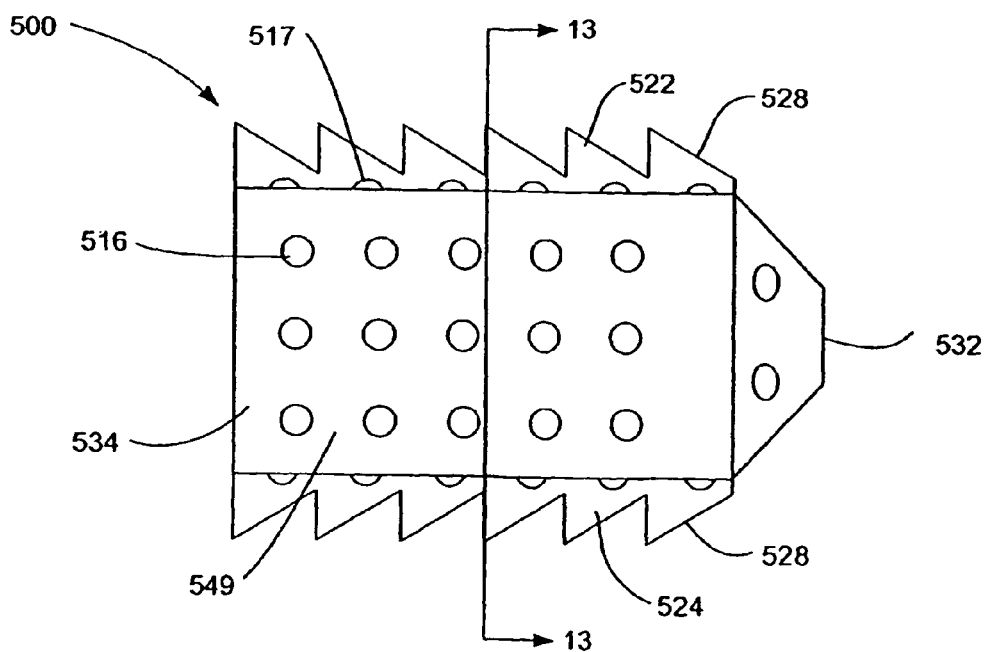
FIG. 12 is a side view of the embodiment of the disclosed implant of the invention depicted in FIG. 11.
Figure 13:
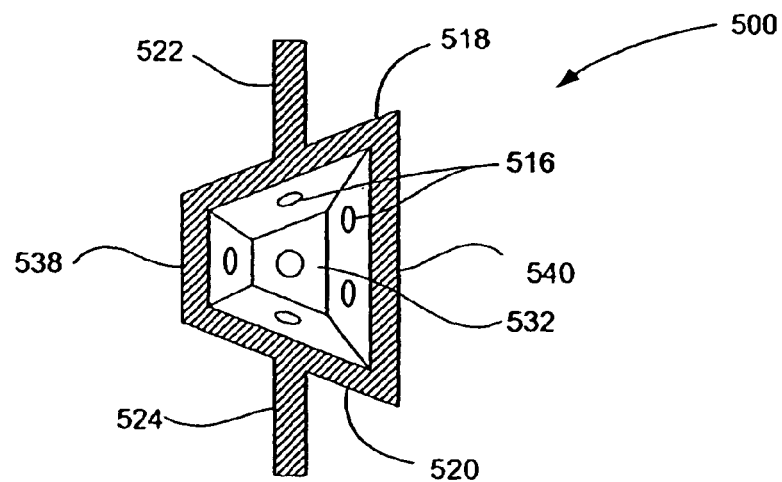
FIG. 13 is a cross-sectional view of the embodiment of the disclosed implant depicted in FIG. 11.

FIGS. 11-13 depict a further embodiment 500 of the disclosed implant. This embodiment 500 is similar to the embodiment 400 in FIGS. 8-10, with the difference being that the narrowest 538 and widest 540 surfaces of embodiment 500 are arranged opposite to their respective positions in embodiment 400. Like embodiment 400, embodiment 500 can be implanted laterally to restore normal curvature to the spine; alternatively, if implanted from an anterior or posterior approach, embodiment 500 would correct lateral curvature of the spine.

Figure 14:
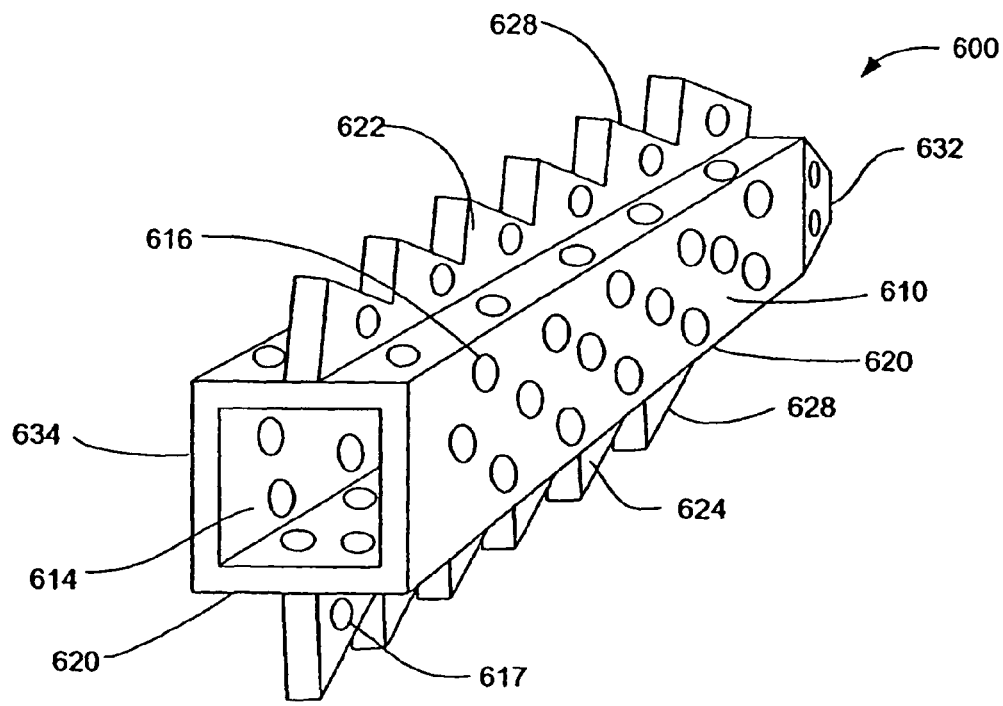
FIG. 14 is a perspective view of a further embodiment of the disclosed implant of the invention.
Figure 15:
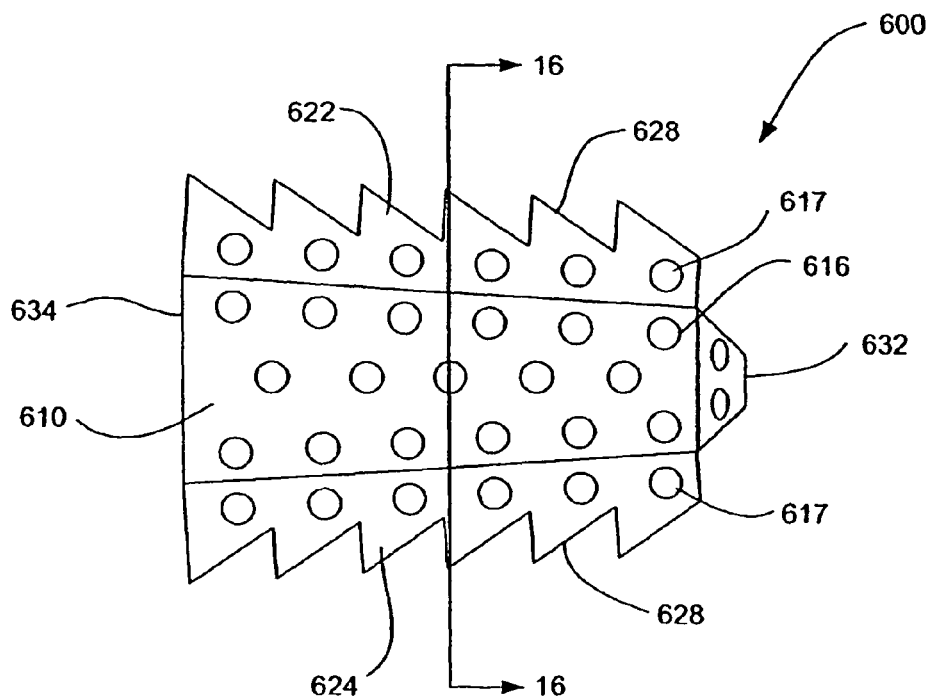
FIG. 15 is side view of the embodiment of the disclosed implant depicted in FIG. 14.
Figure 16:
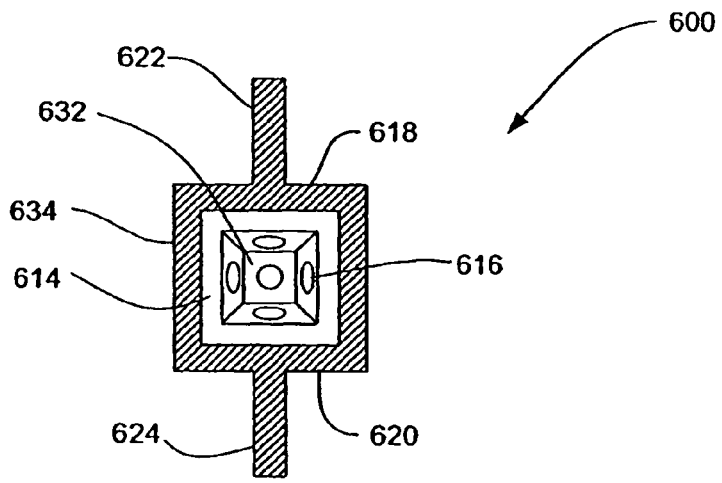
FIG. 16 is a cross-sectional view of the embodiment of the disclosed implant depicted in FIG. 14.

As discussed above, scoliosis, or abnormal lateral curvature of the spine, can also be corrected by positioning a wedge-shaped implant with keels in the intervertebral space. The implant can be constructed for different angles of correction, as with the implant for correcting loss of normal curvature. FIGS. 14-16 depict an embodiment 600 of the disclosed invention that is wedge-shaped for correcting scoliosis, or abnormal lateral curvature, when implanted from a lateral approach. Rather than having narrowest and widest surfaces parallel to the longitudinal axis of the cage, the cage instead is wider at the trailing end 634 of the cage 610 and narrower at the tapered leading end 632. The cage 610 thus is wedge-shaped in a plane that is parallel to the longitudinal axis of embodiment 600. It should be understood that if the embodiment 600 is implanted from a posterior or anterior approach, it would correct loss of lordotic curvature of the spine, rather than correct abnormal lateral curvature.

As with the other embodiments already disclosed and described, the cage 610 includes a hollow interior 614. The hollow interior 614 is adapted to receive and contain any one or combination of the bone growth-promoting materials and substances described above.

Also with the other embodiments, the cage 610 can be roughened and/or covered with bone growth-promoting substances. The surfaces of the cage 610 alternatively can have a plurality of apertures 616. Either measure alone, or both in combination, induce bone growth and integration of the cage 610 into the adjacent vertebrae to be fused.

The implant 610 has at least one keel 622 on the superior surface 618 of the cage 610, and at least one keel 624 on the inferior surface 620 of the cage 610. The keels 622, 624, like the cage 610, can also have a plurality of apertures 617. The keels 622, 624 and the cage 610 can be made of any one or any combination of the materials as described above. They further can have projections or teeth 628 that are oriented to prevent backward expulsion of the implant from the intervertebral space. Moreover, as with the other embodiments, the keels 622, 624 need not run the full length of the elongated/longitudinal axis of the implant 600. Instead, they can be shorter. There can be a plurality of keels 622, 624 projecting in a star-like pattern from the surface of the cage, as in FIG. 3A. In addition, or in the alternative, the keels 622, 624 can be T-shaped or cross-shaped in cross-section substantially perpendicular to the longitudinal axis of the cage, as depicted in FIG. 3B. All of the keels 622, 624 are intended to anchor the implant 600 in the cancellous bone of the vertebral bodies. As such, the keels 622, 624 can provide instant stability and therefore, the correction to reduce or eliminate abnormal lateral curvature is immediate.

Figure 17:
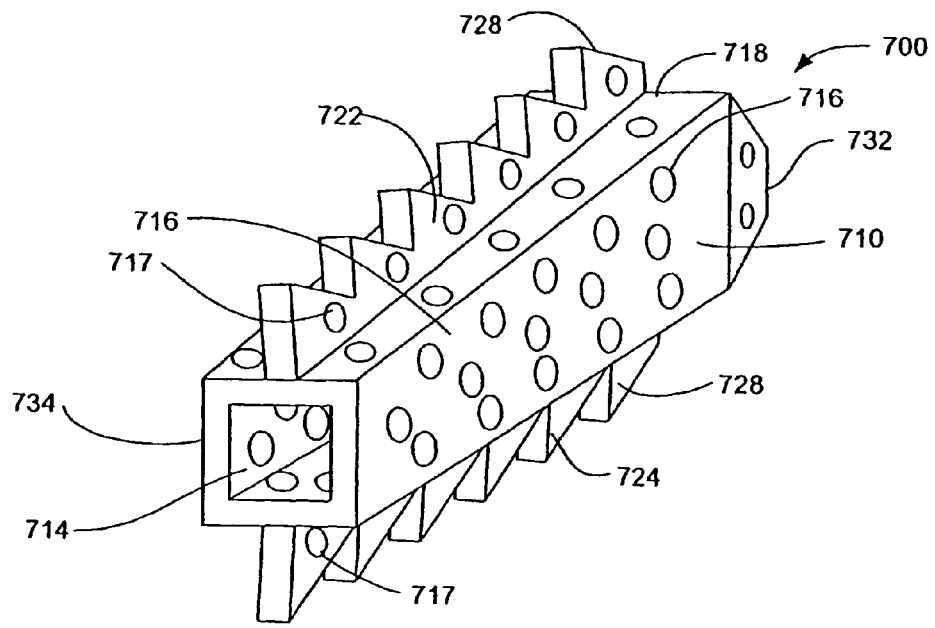
FIG. 17 is a perspective view of a further embodiment of the disclosed implant of the invention.
Figure 18:
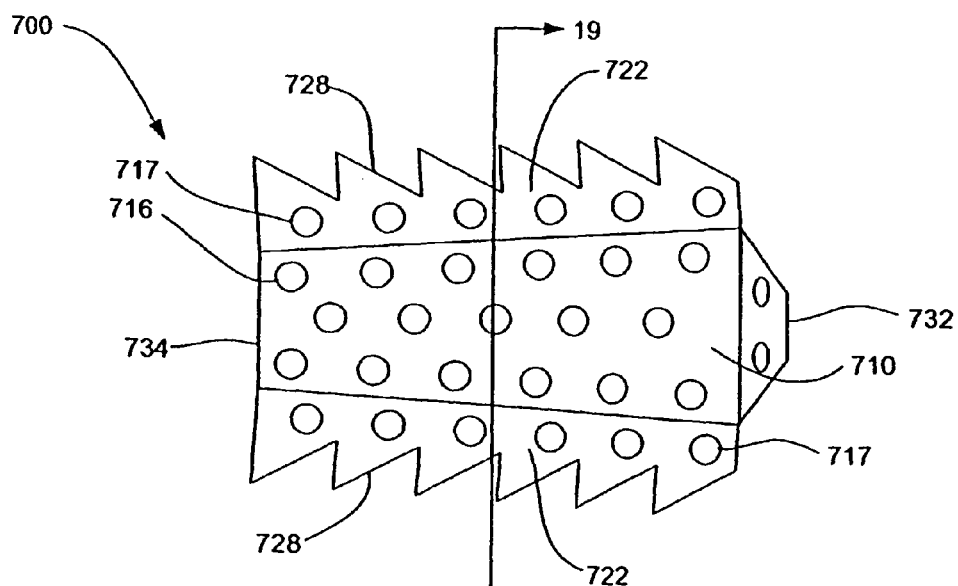
FIG. 18 is a side view of the embodiment of the disclosed implant depicted in FIG. 17.
Figure 19:
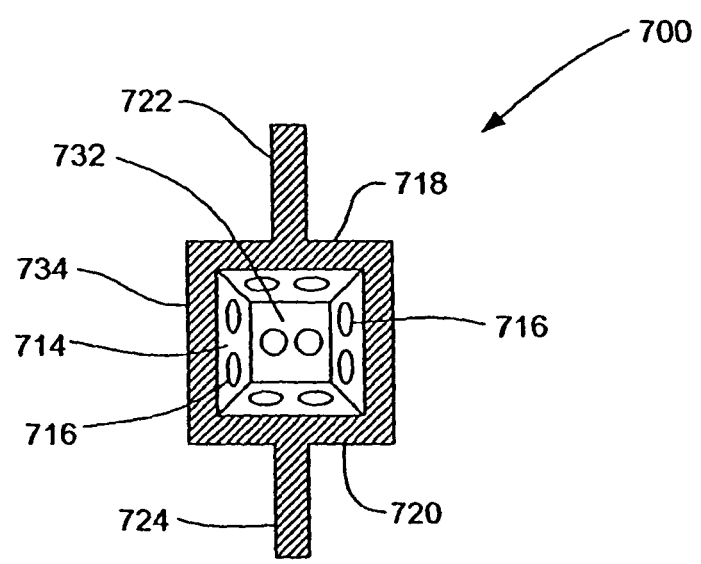
FIG. 19 is a cross-sectional view of the embodiment of the disclosed implant depicted in FIG. 17.

FIGS. 17-19 depict an embodiment 700 of the disclosed invention that also is wedge-shaped, for correction of scoliosis. Embodiment 700 is different from embodiment 600, since the cage 710 of embodiment 700 is intended to correct the opposite lateral curvature. However, it should be understood that, as with embodiment 600, implantation of embodiment 700 from a posterior or anterior approach could be used to restore normal lordotic curvature to the spine.

The cage 710 can be a wedge-shape with rounded edges, as if formed from a cage shaped like a cylinder, or with corners, as if formed from a cage shaped like a rectangular box. As in all of the other embodiments described herein, the cage includes a hollow interior 714 adapted to hold bone growth-promoting materials that encourage bony ingrowth from the vertebral bodies through the cage. The hollow interior 714 can be packed with any one or any combination of the bone growth-promoting substances described herein above.

Also as with other embodiments described herein, the cage 710 can have at least one keel, said keel to have a plurality of apertures 717. The keels 722, 724, located substantially on the superior 718 and inferior 720 surfaces of the cage 710, can run the entire longitudinal length of the cage 710, or they can be shorter. They also can be arrayed in a star-like pattern, as depicted in FIG. 3A. Alternatively or additionally, the keels 722, 724 can have an extension (not shown) at the end of the keel distal to the surface of the cage 710 that makes the keel T-shaped or cross-shaped in cross-section substantially perpendicular to the vertical axis of the keel. This embodiment is depicted in FIG. 3B.

The cage 710 and keels 722, 724 as with all of the embodiments described herein, can be made of any one or any combination of materials described above. The cage 710 and keels 722, 724 can be roughened and/or have apertures 716 and/or be covered or coated with bone growth-inducing substances to induce bone growth and integration of the cage 710 into the adjacent vertebrae to stabilize the affected spine.

Figure 20:
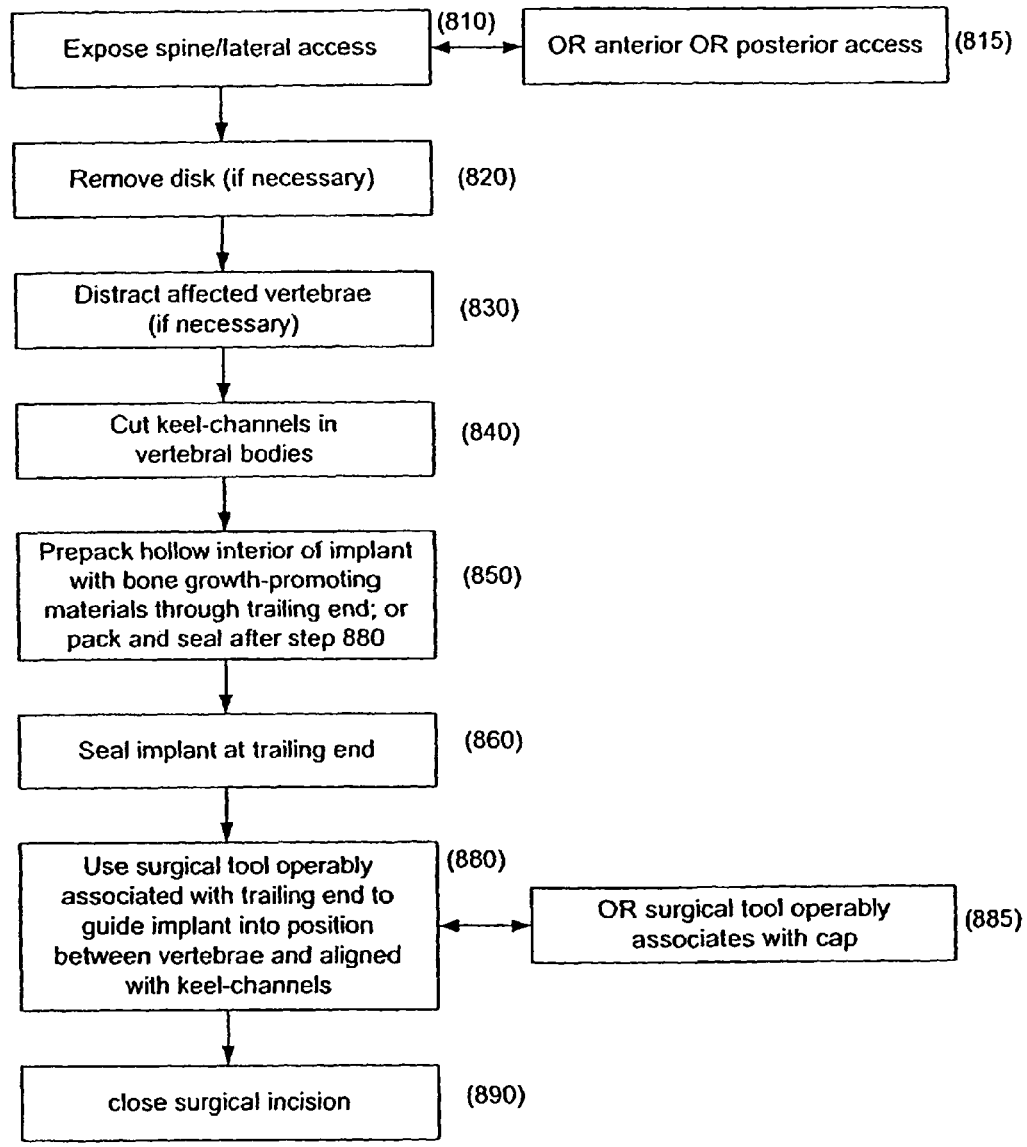
FIG. 20 is a block diagram showing the method steps of the invention for the lateral implantation of an embodiment of the disclosed the implant of the invention.

FIG. 20 is a block diagram showing the basic steps of the disclosed method of the invention of laterally inserting the disclosed implant of the invention in the spine. However, it should be noted at the outset that all embodiments of the disclosed implant can be implanted not only from a lateral approach, but also from either an anterior or posterior approach, using the appropriate surgical technique and instruments. Preferably the embodiments of FIGS. 17-19 are inserted with a posterior approach or an anterior approach. The anterior and posterior approaches are well-known.

First, 810 the spine is exposed through a lateral access. However, it is also within the scope of the disclosed method to access the spine from an anterior or posterior approach 815, using an appropriate well-known technique. Next, the affected intervertebral disk is removed if necessary 820, and the two vertebrae to be fused are distracted apart, if necessary 830. As before, it is also contemplated that these steps can occur from a posterior or anterior approach.

Keel-receiving channels next are cut into at least one of the affected vertebrae, using a wedge- or chisel-shaped surgical instrument adapted to penetrate the cortical bone and into the cancellous bone of the vertebral bodies 840. The number of keel-receiving channels to be cut and their position will be determined by the number and configuration of the keels on the selected embodiment of the disclosed implant. It may also be necessary to use an appropriate surgical tool to shape the vertebral bones to accommodate the implant 850.

Either before or after the implant is inserted between the vertebral bodies, bone and/or bone growth-promoting materials are packed into the hollow interior of the implant through the open second end of the cage that is the trailing end, distal to the tapered leading end 860. The implant then is sealed 870 at its trailing end. A cap can be used to close off the trailing end, and the trailing end 880 or the cap 885 can be adapted operably to associate with a surgical instrument that can be used to guide the implant into the intervertebral space. While the implant is guided into position, the keels are aligned with the keel-receiving channels cut into the vertebral bodies 880. Once the implant is properly positioned and the procedure is complete, the surgical incision is closed.

Additional steps, such as additional distraction from different approaches, can also be performed without departing from the scope of what is disclosed. It is to be understood that any of the embodiments can be inserted laterally, that is substantially perpendicularly to the sagittal plane of the patient. The implants also can be inserted along a posterior/anterior line, with some implants preferably inserted from the posterior and some inserted from an anterior direction. For example, the implants of FIGS. 1-13 preferably are inserted from a lateral direction. The implants depicted in FIGS. 14-16 are preferably inserted from a posterior direction. FIGS. 17-19 are preferably inserted from an anterior direction.

Figure 23:
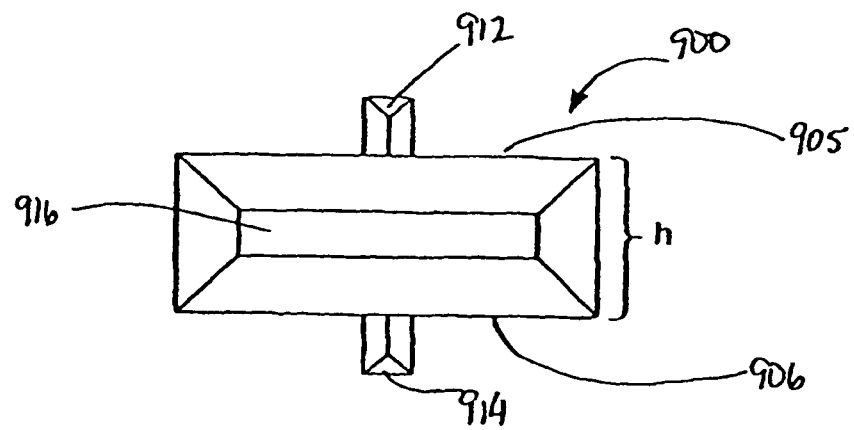
FIG. 23 is a distal end view of the embodiment of the disclosed keel-receiving channel cutting tool depicted in FIG. 20.

In addition to disclosure of embodiments of a fusion implant, tools for preparing and inserting an implant are also disclosed. FIGS. 21-23 show an embodiment of a tool for preparing vertebral bodies to receive any of the implants discussed above, while FIGS. 24-27 show an embodiment of an implantation tool for inserting embodiments of the disclosed implants.

FIGS. 21-23 are the top view, the side view, and an end view of the keel-receiving channel cutting tool 900. The cutting tool 900 has a handle 910 at its proximal end for controlling the tool during operation. As will be appreciated by those of skill in the art, the handle 910 can be removable or affixed to the cutting end. The distal end 902 of the tool 900 is a solid head that has an upper surface 905, and a lower surface 906. The upper surface 905 has a first blade 912 mounted thereon, and the lower surface 906 has a second blade 914 mounted thereon. Preferably the first blade 912 is about centered with the upper surface 905, and the second blade 914 is about centered with the lower surface 906. The first and second blades 912, 914 are oriented to cut a space in a first and second intervertebral body to receive a keel on the inferior and superior surfaces of an implant. The space is perpendicular to the sagittal plane of the vertebrae, and allows for the lateral insertion of the implant. FIG. 23 is a view of the distal end of the cutting tool 900 showing the beveled end 916 and the first and second blades 912, 914. The height h of the head 902 of the cutting tool 900 (shown in FIG. 23) approximates the distance between two vertebral bodies or the height of the disk space. In this embodiment of cutting tool 900, the blades 912, 914 extend above and below the head 902.

As will be appreciated by those of skill in the art, the tool shown in FIG. 21 can be modified such that instead of cutting keel-receiving channels in the upper and lower vertebral bodies at the same time, two tools are provided so that only one vertebral body is cut for keel-receiving channels at a time. For example, an alternative embodiment of cutting tool 900 has a first tool with a single blade mounted on the head 902. A second tool could be provided having a single blade mounted on the head 902, and additionally on the opposing surface, a guide. The guide on the surface opposite the surface with the blade is designed to engage with the first keel-receiving channel cut the first vertebrae with the first tool to ensure that the second cut is optimally aligned with the first cut.

It is to be further appreciated by those of skill in the art that the blades 912, 914 can be T- or cross-shaped, to cut keel-receiving channels adapted to receive T- or cross-shaped keels, as for the embodiment of implant of the invention depicted in FIG. 3B. It is further to be understood that the blades 912, 914 can be arrayed to cut keel-receiving channels that could receive keels arrayed in a somewhat star-like configuration, as depicted in FIG. 3A. Other arrays of the blades 912, 914 to prepare keel-receiving channels for different implants with various keel configurations also can be appreciated by one of ordinary skill in the art.

Figure 24:
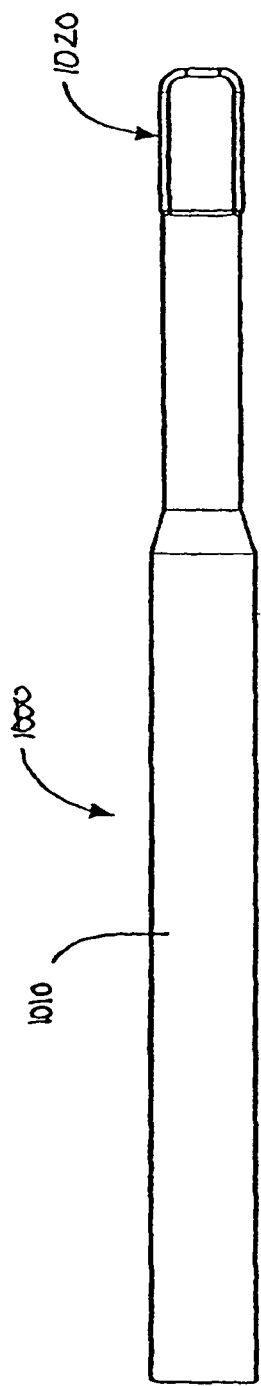
FIG. 24 is a side view of an embodiment of a disclosed implantation tool.
Figure 25:
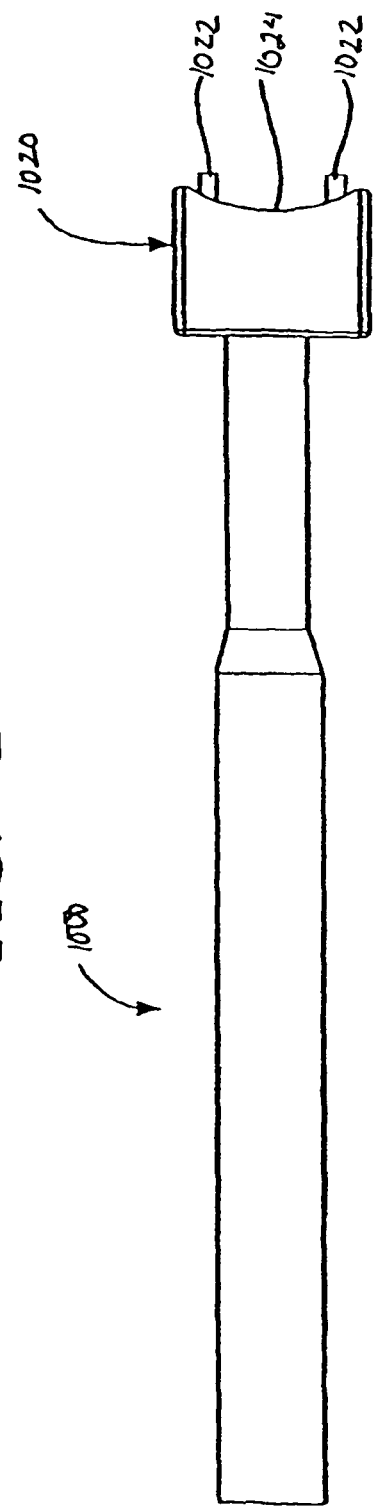
FIG. 25 is a top view of the embodiment of the disclosed implantation tool depicted FIG. 24.
Figure 26:
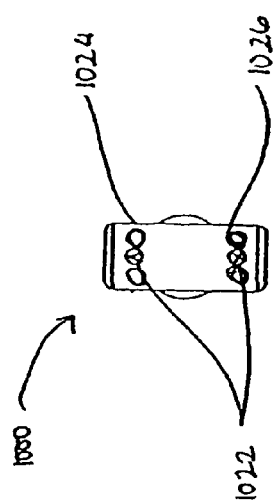
FIG. 26 is a front view of the embodiment of the disclosed implantation tool depicted in FIG. 24.
Figure 27:
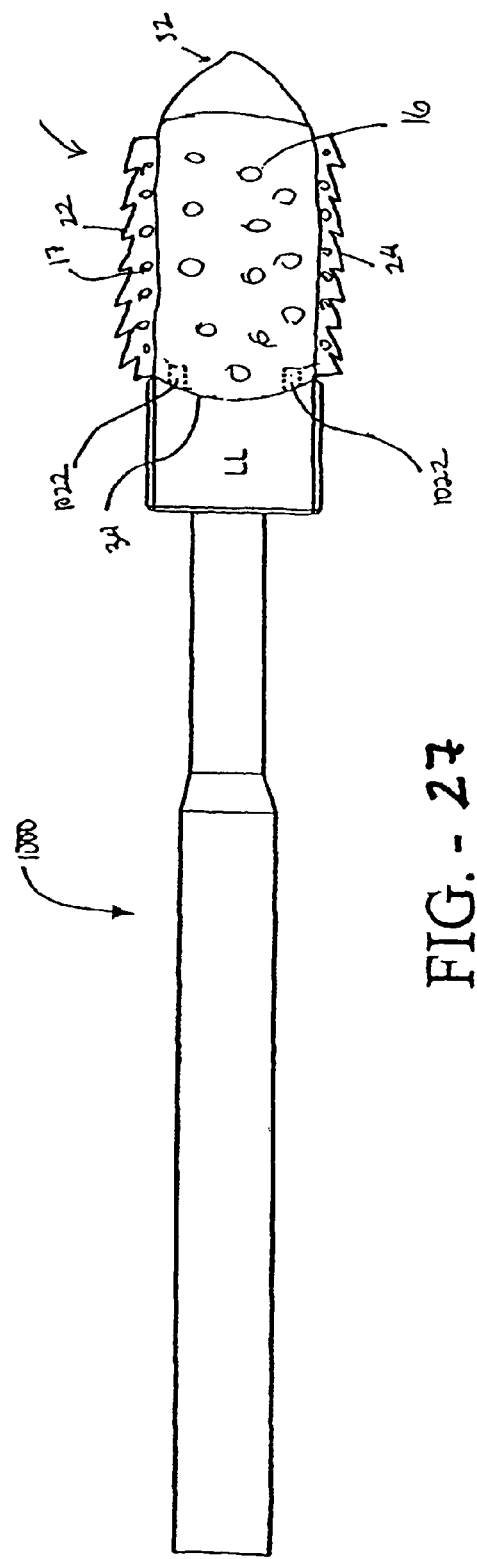
FIG. 27 is a top view of the embodiment of the disclosed implantation tool depicted in FIG. 24, as it engages an embodiment of the disclosed implant of the invention.

FIGS. 24-27 depict the implanting tool used to insert an implant, such as those embodiments disclosed herein, between vertebral bodies. FIG. 24 is a side view of the implantation tool 1000 that has a handle 1010 and an implant holder 1020. The implant holder 1020 has an implant contacting surface 1024 and at least one pin 1022, shown in FIG. 25, for engaging the trailing end of an implant. The contacting surface 1024 can be shaped to conform to any shape given to the trailing end of the implant. The implant nests within a contacting surface 1024 and is held by pins 1022. FIG. 26 shows the distal view of the end of the tool with two pins 1022 for securing the implant. FIG. 27 shows how the pins 1022 would engage the trailing end of an implant, such as implant 100 depicted in FIG. 3.

A variety of kits can be assembled that include an implant selected for a particular patient. The kit could also include several cutting tools 900 and several implanting tools 1000 or a single handle that cooperates with cutting ends 902 and implantation ends 1020.

Figure 28:
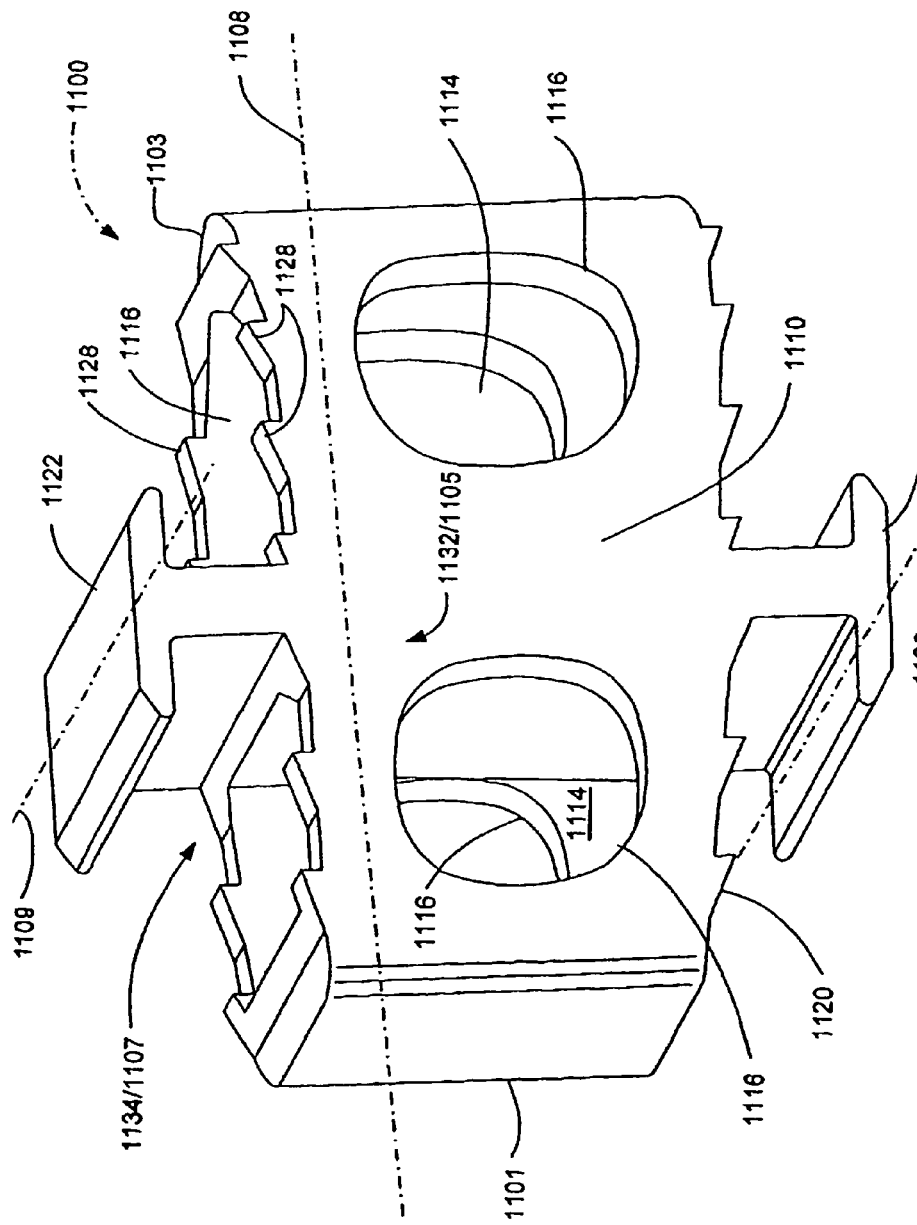
FIG. 28 is a perspective view of a further embodiment of the disclosed implant of the invention.
Figure 29:
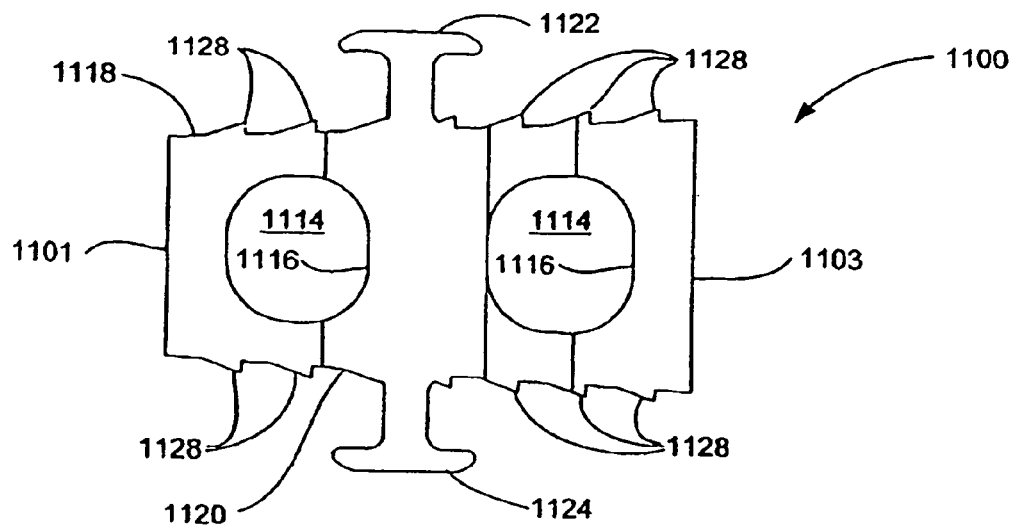
FIG. 29 is a side view of the embodiment of the disclosed implant of the invention shown in FIG. 28.
Figure 30:
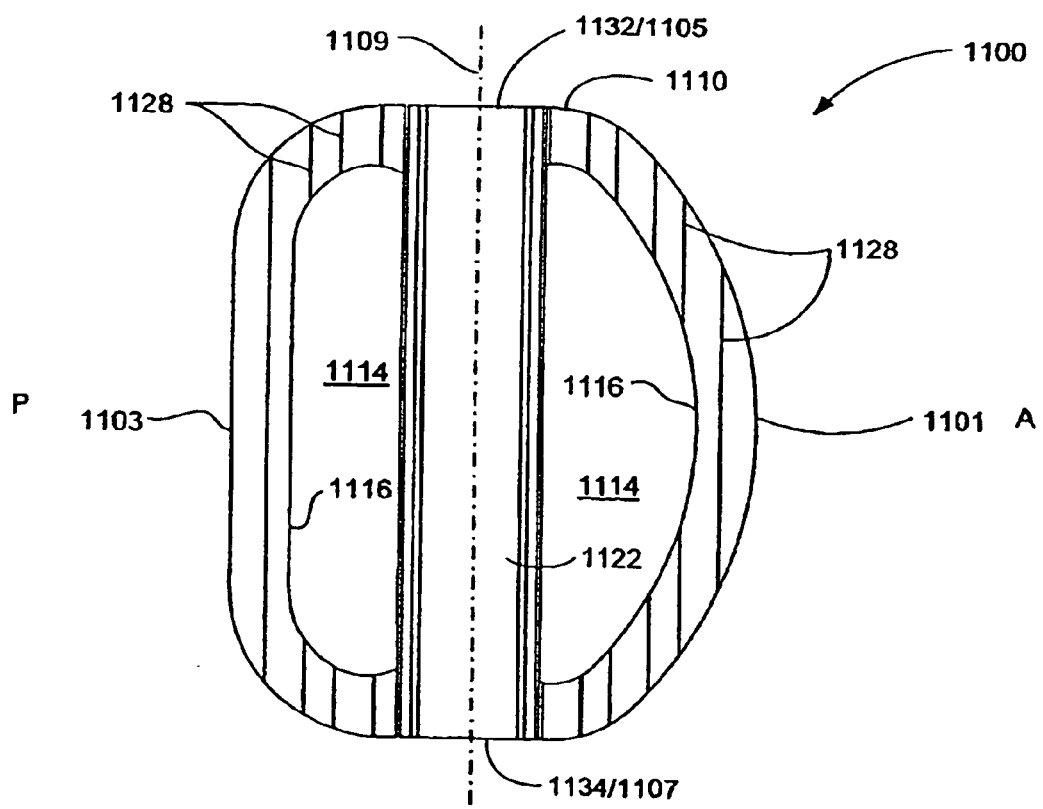
FIG. 30 is a top view of the embodiment of the disclosed implant depicted in FIG. 28.

FIGS. 28-30 depict a further embodiment 1100 of the disclosed implant, which is intended to be implanted from a lateral surgical approach between adjacent vertebral bodies that are to be fused.

Embodiment 1100 has a cage 1110 that is D-shaped from a top-view of the implant 1100, as depicted in FIG. 30. The curved side or segment 1101 of the D-shape is the side of the implant 1100 that will be oriented anteriorly, during lateral implantation and once implanted, because the curved segment 1101 corresponds to the rounded anterior side of the vertebral body. The substantially straight segment of the D-shape 1103 is located at the opposite and posterior side of the implant 1100.

The implant 1100 has a leading end 1132 and a trailing end 1134. The leading end 1132 is the first part of the implant 1100 to be inserted into the intervertebral space, and is oriented so that the curved side 1101 of the D-shape of the implant 1100 corresponds to the curved anterior of the vertebral bodies when the implant 1100 is positioned. For ease of insertion, the leading end 1132 can be tapered.

The cage 1110 has at least one keel that stabilizes the affected spine upon implantation and thus increases the likelihood of a successful fusion. Each keel fits into a keel-receiving channel that is cut through the vertebral bone endplate and into the cancellous bone of the vertebral body, exposing the cancellous bone. Exposing the cancellous bone puts this tissue in communication with bone growth-promoting materials inside the cage 1110, as explained further below, which promotes bone fusion.

In a preferred embodiment, the first keel 1122 extends from a superior surface 1118 of the cage 1110, which superior surface 1118 faces the upper vertebra of the vertebrae to be fused, and a second keel 1124 extends from an inferior surface 1120 of the cage 1110, which inferior surface 1120 faces the lower of the two vertebrae to be fused. The longitudinal axis 1109 of the keels 1122, 1124 is substantially perpendicular to an axis 1108 drawn from the anterior end of the implant 1100 (i.e., the end that contains the curved side of the D-shape 1101) to the posterior end of the implant 1100 (i.e., the end that contains the substantially straight side of the D-shape 1103). Accordingly, as the implant 1100 is implanted, the keels 1122, 1124 enter along their longitudinal axis 1109. The longitudinal axis 1109 of the keels 1122, 1124 is substantially perpendicular to the sagittal plane of the patient.

In a preferred embodiment, the keels 1122, 1124 are T-shaped or cross-shaped, viewed in cross-section substantially perpendicular to the axis 1108 running from the anterior and posterior ends of the implant 1100. The T-shape can contribute further to the stability of the affected spine by providing additional surface area upon which the cancellous bone can rest. It should be appreciated by one skilled in the art that there can be a plurality of keels which can be variously arrayed or configured over the superior 1118 and inferior 1120 surfaces of the cage 1110. The keels further can have a plurality of apertures 1117 (not shown) to promote bony ingrowth.

The cage 1110 has a hollow interior 1114 adapted to contain at least one bone growth-promoting material. The hollow interior 1114 is adapted to contain a bone graft or other bone growth-promoting material, to initiate formation of a bony fusion mass between two affected vertebrae. The bone growth-promoting materials can include, but are not limited to, naturally occurring bone, bone chips, processed bone, synthetic bone, hydroxyapatite, calcium phosphate compounds, naturally occurring bone morphogenic proteins, natural, synthetic, and recombinant bone morphogenic proteins, growth factors, and cytokines. The hollow interior 1114 of the cage 1110 is in communication with the exterior of the cage 1110, where the cancellous bone of the vertebral bodies has been exposed, through a plurality of apertures 1116 that fully penetrate the surface of the cage.

In a preferred embodiment, the superior 1118 and inferior 1120 surfaces of the cage 1110 are substantially open to hollow interior 1114 because the apertures 1116 on either side of the keels 1122, 1124 are broad. The keels 1122, 1124 are embedded in the cancellous bone of the vertebral bodies, which causes the open superior 1118 and inferior 1120 surfaces of the cage 1110 to abut the vertebral bodies and brings the bone growth-promoting materials in the hollow interior 1114 of the cage 1110 into direct and intimate contact with the exposed cancellous bone. The apertures 1116 in the superior 1118 and inferior 1120 surfaces of the cage 1110 need not be capped because they abut the vertebral bodies. Moreover, the implant 1100 is made of materials that resist compression, as described further below, and therefore compressive forces on the spine will not cause exudation or migration of the bone growth-promoting materials from the hollow interior 1114 through those apertures 1116.

In a preferred embodiment, additional apertures 1116 are configured on the leading 1132 and trailing 1134 ends. The apertures 1116 on the trailing end 1134 can be used to pack the hollow interior 1114 of the implant 1100 with at least one bone-growth promoting material during implantation surgery. Alternatively, the hollow interior 1114 can be prepacked before surgery. These apertures 1116 can be sealed with a cap (not shown) or also left open.

The superior 1118 and inferior 1120 surfaces of the cage 1110 can have a plurality of projections or teeth 1128 that can penetrate the vertebral endplates. The projections or teeth 1128 are oriented to prevent posterior expulsion of the implant 1100 from the intervertebral space. The projections or teeth 1128 can penetrate at least partially the vertebral endplate and thus can enhance anchoring of the implant to prevent expulsion.

The projections or teeth 1128 also can serve a dual function. By engaging the vertebral bones, the projections or teeth 1128 can further enhance bone healing and bony fusion of the vertebral bodies. Thus, by exposing fresh bone of the vertebral bodies, the penetration of the vertebral bones by the projections or teeth 1128 can further stimulate bone healing, in addition to the healing reaction set in motion by cutting keel-receiving channels and providing bone growth-promoting materials in the hollow interior 1114 of the cage 1110.

The cage 1110 also can have at least one hole (not shown) in the trailing end 1134, adapted to receive a mating pin component extending from a surgical implantation tool. The pin and the hole can be paired operably to connect the implant with the implantation tool. The tool with the connected implant then is used to position the implant between the vertebral bodies that are to be stabilized through implantation surgery and fused.

It should be appreciated that the shape of the cage 1110 can be varied either to correct for loss of normal lordotic curvature of the spine, or to correct for scoliosis (excessive lateral curvature of the spine). The cage 1110 can be wedge-shaped, to correct scoliosis, with the wedge being narrower at the leading end 1132 and broader at the trailing end 1134. The implant 1100 can be implanted from either side of the patient to correct scoliosis. The appropriate side depends upon the lateral curvature that is to be corrected while accomplishing interbody fusion.

Alternatively, the cage 1110 can be wedge-shaped in a manner that will correct loss of normal lordotic curvature. To restore normal curvature, the wedge of the cage 1110 would be oriented in a plane that is parallel to the axis 1108 between the anterior and posterior sides of the implant 1100.

The implant 1100 can be made from a variety of materials, including but not limited to bioceramics; calcium phosphate ceramics, such as hydroxyapatite tricalcium phosphate, tetracalcium phosphate, α-calcium pyrophosphate, β-calcium pyrophosphate and mixtures thereof; and ceramic/growth factor composites, such as ceramic/bone morphogenic protein ("BMP") composite (made with any BMP, whether natural, synthetic, or recombinant). The implant also can be made of medical grade titanium, stainless steel or cobalt chrome. Other materials that have appropriate structural strength and that are suitable for implantation into a patient can also be used.

One other class of materials contemplated for use is the class of biocompatible polymers. Copolymers, blends and composites of polymers are also contemplated for fabrication of parts of the disclosed device. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer.

One group of biocompatible polymers is the polyaryl ester ketones which has several members, which include polyetheretherketone (PEEK), and polyetherketoneketone (PEKK). PEEK has proven as a durable material for implants, as well as meeting criteria of biocompatibility. Medical grade PEEK is available from Victrex Corporation under the product name PEEK-OPTIMA. Medical grade PEKK is available from Oxford Performance Materials under the name OXPEKK, and also from CoorsTek under the name Bio-PEKK. Still another interesting group of biocompatible polymers is the polyalkyl biocompatible polymers, such as polyethylenes, polypropylenes, and the like.

These medical grade biocompatible polymers also are available as reinforced polymer materials. To reinforce a polymeric material, fillers are added to a polymer, copolymer, polymer blend, or polymer composite. Fillers are added to modify properties, such as mechanical, optical, and thermal properties. In this case, fillers, such as carbon fibers, are added to reinforce the polymers mechanically to enhance strength for certain uses, such as load bearing devices.

Figure 31:
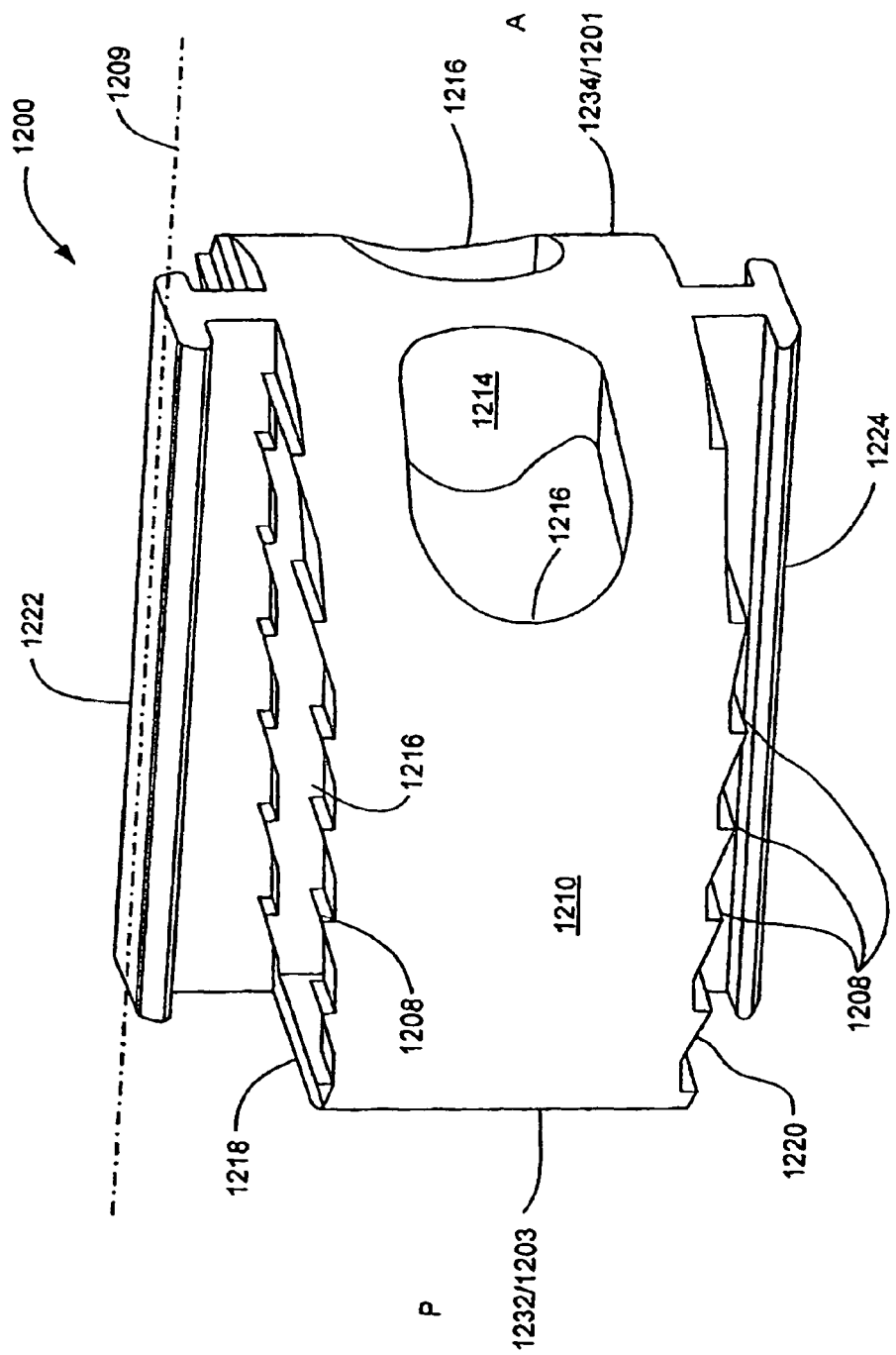
FIG. 31 is a perspective view of an embodiment of the disclosed implant of the invention.
Figure 32:
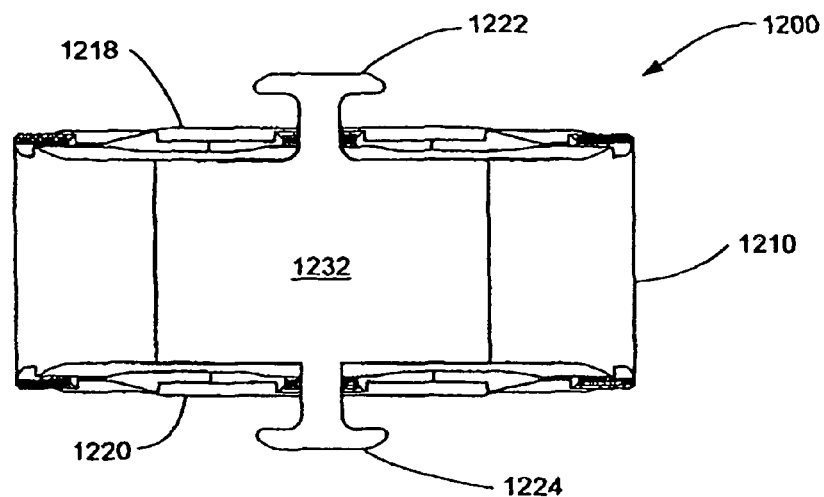
FIG. 32 is a side view of the embodiment of the disclosed implant of the invention depicted in FIG. 31.
Figure 33:
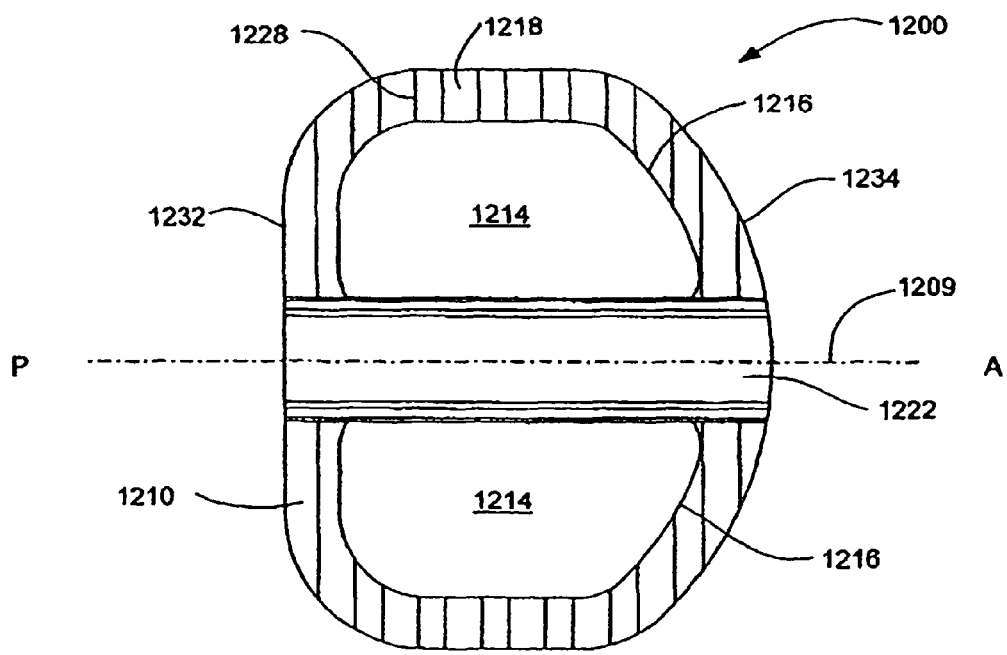
FIG. 33 is a is a top view of the embodiment of the disclosed implant depicted in FIG. 31.

FIGS. 31-33 depict a further embodiment 1200 of the disclosed implant of the invention. This embodiment 1200 is for implantation from an anterior surgical approach. Accordingly, the posterior end of the implant is the leading end 1232, or the end that is first inserted into the intervertebral space, and the anterior end of the implant is the trailing end 1234.

Similar to cage 1110, cage 1210 is D-shaped from a top view (FIG. 33). The side that is curved like the curved side of the D-shape 1201 is the trailing/anterior end 1234 of the implant 1200 that will be positioned anteriorly in the patient's body when implanted from an anterior approach. The substantially straight side of the D-shape 1203 corresponds to the leading/posterior end 1232 of the implant 1200 that will be positioned posteriorly in the patient's body when implanted from an anterior approach. For ease of insertion, the leading end 1232 can be tapered.

The cage 1210 has at least one keel, like the cage 1110. As discussed above, each keel is received into a keel-receiving channel cut with a "T"-shaped cutter into the cancellous bone of a vertebral body during surgery with a keel-receiving channel cutting tool. In a preferred embodiment having two keels 1222, 1224, a first keel 1222 extends from the superior surface 1218 of the cage 1210, and a second keel 1224 extends from the inferior surface 1220 of the cage 1210. The longitudinal axis 1209 of the keels 1222, 1224 is parallel with an axis 1108 extending from the anterior/trailing end 1234 to the posterior/leading end 1132 of the implant 1200. In other words, the keels 1222, 1224 extend from the anterior/trailing end 1234 to the posterior/leading end 1232 of the implant 1200. Accordingly, when the implant 1200 is inserted during surgery, the keels 1222, 1224 enter the intervertebral space in a direction parallel to the longitudinal axis 1209 of the keels 1222, 1224, and to the axis from the posterior/leading end 1232 and the anterior/trailing end 1234.

It should be appreciated that for implants 1100 and 1200, the keels need not extend the full length of the cage in the direction of their orientation. As with implant 1100, the implant 1200 can have keels that are configured in different ways over the surface(s) of the implant 1200.

A preferred embodiment has keels 1222, 1224 that are T-shaped when viewed in cross-section substantially perpendicular to the longitudinal axis 1209 of the keels 1222, 1224.

The cage 1210 has a hollow interior 1214 that is adapted to contain at least one of the bone growth-promoting materials set forth above. The hollow interior 1214 is in communication with the exterior of the cage 1210 through a plurality of apertures 1216 that fully penetrate the surface of the cage 1210. In a preferred embodiment, the superior 1218 and inferior 1220 surfaces of the cage 1210 are substantially open to the hollow interior 1214 because the apertures 1216 on either side of the keels 1222, 1224 are broad. The keels 1222, 1224 are embedded in the cancellous bone of the vertebral bodies, which causes the open superior 1218 and inferior 1220 surfaces of the cage 1210 to abut the vertebral bodies and brings the bone growth-promoting materials in the hollow interior 1214 into direct and intimate contact with the exposed cancellous bone. The apertures 1216 in the superior 1218 and inferior 1220 surfaces of the cage 1210 need not be capped because they abut the vertebral bodies. Moreover, the implant 1200 is made of materials discussed above that resist compression, and therefore protect the materials in the hollow interior 1214 from expulsion from the implant 1200.

In a preferred embodiment, additional apertures 1216 are configured on the trailing end 1234. Apertures 1216 also can be located on the leading end 1232. The trailing end apertures 1216 can be used to pack bone growth-promoting materials into the hollow interior 1214 during surgery, particularly after the implant 1200 is positioned. Alternatively, the hollow interior 1214 of the implant 1200 can be pre-packed and implanted. The apertures 1216 can be sealed with a cap (not shown) or also left open.

The superior 1218 and inferior 1220 surfaces of the cage 1210 can have a plurality of projections or teeth 1228 that can penetrate the vertebral endplates and that are oriented to prevent backward expulsion of the implant. As discussed above, the projections or teeth 1228 further promote bony fusion.

As above for implant 1100, the trailing end 1234 of implant 1200 can have at least one hole adapted to mate with at least one pin on an implantation tool. The tool is thus operably connected with the implant 1200 and used to position the implant 1200 in the intervertebral space during implantation surgery.

As discussed above, the shape of the cage 1210 can be varied to correct for loss of lordotic curvature or to correct lateral curvature of the spine. To correct lateral curvature of the spine, the cage 1210 can be wedge-shaped with the wedge oriented in a direction perpendicular to the longitudinal axis 1209 of the keels 1222, 1224 and axis 1208 between the anterior/trailing end 1234 and posterior/leading end 1232. To correct loss of normal curvature of the spine, the wedge can be oriented in a direction parallel to axis 1208 and axis 1209.

The cage can be made of any of the materials discussed at length above for embodiment 1100.

What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the embodiments described herein, thereby enabling others skilled in the art to understand the various embodiments and various modifications that are suited to the particular use contemplated. It is intended that the scope of what is disclosed be defined by the following claims and their equivalence.

What is claimed is:

1. An intervertebral spinal fusion implant comprising:
   a D-shaped body including a peripheral wall that encloses an inner cavity, said peripheral wall having a D-shaped cross-section and including a curved anterior end and an opposite posterior end with an anterior-posterior axis drawn from said curved anterior end to said posterior end, said body having superior and inferior sides with said superior side adapted to engage an upper vertebral body and said inferior side adapted to engage a lower vertebral body, said superior and inferior sides each including an opening communicating with said inner cavity, said peripheral wall defining apertures located on opposite sides of the peripheral wall substantially parallel to said anterior-posterior axis, said apertures communicating with said inner cavity to place said inner cavity in communication with an exterior of said body;
   a rib extending across said inner cavity and including a first end joined to said peripheral wall adjacent said curved anterior end and a second end joined to said peripheral wall adjacent said posterior end; and
   a first keel extending from said rib in a superior direction, a second keel extending from said rib in an inferior direction, and wherein each of said keels extends along a longitudinal axis substantially parallel to said anterior-posterior axis and at least one of said keels has a maximum width that is greater than a minimum width of said rib.

2. The implant of claim 1 wherein said peripheral wall further includes opposite sides extending generally parallel with one another along said anterior-posterior axis from said curved anterior end to said posterior end.

3. The implant of claim 2 wherein said opposite sides are planar.

4. The implant of claim 1 wherein each of said keels has a T-shaped cross section.

5. The implant of claim 1 wherein each of said keels extends from an exterior of said peripheral wall at said curved anterior end to an exterior of said peripheral wall at said posterior end.

6. The implant of claim 1 wherein each of said keels extends along an entire outer dimension of said body along said anterior-posterior axis.

7. The implant of claim 1 wherein said keels are formed integral with said rib to define a single, unitary piece of said body.

8. The implant of claim 1 wherein said superior and inferior sides taper relative to one another to provide said body with a wedge shape.

9. The implant of claim 8 wherein said superior and inferior sides taper relative to one another along said anterior-posterior axis to provide said body with said wedge shape.

10. The implant of claim 9 wherein said superior and inferior sides taper along an entire dimension of said body from said curved anterior end to said posterior end.

11. The implant of claim 8 wherein said superior and inferior sides taper relative to one another in a direction generally perpendicular to said anterior-posterior axis to provide said body with said wedge shape.

12. The implant of claim 8 wherein said superior and inferior sides are substantially planar.

13. The implant of claim 8 wherein said body tapers from a narrower end at one of said anterior and posterior ends to a broader end at the other of said anterior and posterior ends.

14. The implant of claim 13 wherein said body is narrower at said anterior end and broader at said posterior end.

15. The implant of claim 1 wherein said superior and inferior sides each define a plurality of teeth.

16. The implant of claim 1 wherein at least one of said apertures is positioned on each side of said first and second keels.

17. The implant of claim 1 further comprising a bone growth promoting material positioned within said inner cavity, said bone growth promoting material selected from the group of materials consisting of naturally occurring bone, processed bone, synthetic bone, hydroxyapatite, calcium phosphate compounds, naturally occurring bone morphogenic proteins, recombinant bone morphogenic proteins, synthetic bone morphogenic proteins, growth factors, and cytokines.

18. The implant of claim 1 wherein said body is formed of a material selected from the group consisting of bioceramics, calcium phosphate ceramics, chrome cobalt, titanium, stainless steel, biocompatible carbon fiber reinforced polymer, biocompatible polymers, copolymers, and blends and composites of polymers.

19. The implant of claim 18 wherein said body is comprised of a biocompatible polymer including polyaryl ester ketone.

20. The implant of claim 1 wherein said keels are formed integral with said rib.

21. An intervertebral spinal fusion implant comprising:
    a D-shaped body including a peripheral wall that encloses an inner cavity, said peripheral wall having a D-shaped cross-section and including a curved anterior end and an opposite posterior end with an anterior-posterior axis drawn from said curved anterior end to said posterior end, said body having superior and inferior sides with said superior side adapted to engage an upper vertebral body and said inferior side adapted to engage a lower vertebral body, said superior and inferior sides each including an opening communicating with said inner cavity, said peripheral wall defining apertures located on opposite sides of the peripheral wall substantially parallel to said anterior-posterior axis, said apertures communicating with said inner cavity to place said inner cavity in communication with an exterior of said body;

a rib extending across said inner cavity and including a first end joined to said peripheral wall adjacent said curved anterior end and a second end joined to said peripheral wall adjacent said posterior end; and a first keel extending from said rib in a superior direction, a second keel extending from said rib in an inferior direction, and wherein each of said keels has a T-shaped cross section extending along a longitudinal axis substantially parallel to said anterior-posterior axis such that at least one of said keels has a maximum width that is greater than a minimum width of said rib, and wherein said keels are formed integral with said rib.

22. The implant of claim 21 wherein said peripheral wall further includes opposite planar sides extending generally parallel with one another along said anterior-posterior axis from said curved anterior end to said posterior end.

23. The implant of claim 21 wherein each of said keels extends along an entire outer dimension of said body along said anterior-posterior axis from an exterior of said peripheral wall at said curved anterior end to an exterior of said peripheral wall at said posterior end.

24. The implant of claim 21 wherein said superior and inferior sides taper relative to one another to provide said body with a wedge shape.

25. The implant of claim 24 wherein said superior and inferior sides taper relative to one another along said anterior-posterior axis to provide said body with said wedge shape.

* * * * *